US009095562B2

(12) United States Patent
Centeno et al.

(10) Patent No.: US 9,095,562 B2
(45) Date of Patent: Aug. 4, 2015

(54) METHODS AND COMPOSITIONS FOR OPTIMIZED EXPANSION AND IMPLANTATION OF MESENCHYMAL STEM CELLS

(75) Inventors: Christopher J. Centeno, Westminster, CO (US); Cristin Keohan, Westminster, CO (US)

(73) Assignee: Regenerative Sciences, Inc., Broomfield, CO (US)

( * ) Notice: Subject to any disclaimer, the term of this patent is extended or adjusted under 35 U.S.C. 154(b) by 273 days.

(21) Appl. No.: 11/773,774

(22) Filed: Jul. 5, 2007

(65) Prior Publication Data
US 2009/0010896 A1 Jan. 8, 2009

(51) Int. Cl.
A61K 35/12 (2006.01)
C12N 5/06 (2006.01)
A61K 35/28 (2006.01)
C12N 5/0775 (2010.01)

(52) U.S. Cl.
CPC .............. A61K 35/28 (2013.01); C12N 5/0663 (2013.01); A61K 2035/124 (2013.01); C12N 2502/115 (2013.01)

(58) Field of Classification Search
CPC ................. C12N 2502/115; C12N 2502/1352; C12N 2502/1358; C12N 5/0675; C12N 5/0663; A61K 35/19; A61K 35/28; A61K 2035/124
See application file for complete search history.

(56) References Cited

U.S. PATENT DOCUMENTS

| 4,832,044 A | 5/1989 | Garg |
| 5,145,676 A | 9/1992 | Fahey et al. |
| 5,165,938 A | 11/1992 | Knighton |
| 5,198,357 A | 3/1993 | Holmovist et al. |
| 5,226,914 A * | 7/1993 | Caplan et al. ................. 435/325 |
| 5,486,359 A | 1/1996 | Caplan et al. |
| 5,693,341 A | 12/1997 | Schroeder et al. |
| 5,736,396 A | 4/1998 | Bruder et al. |
| 5,749,874 A | 5/1998 | Schwartz |
| 5,769,899 A | 6/1998 | Schwartz et al. |
| 5,770,215 A | 6/1998 | Moshyedi |
| 5,842,477 A | 12/1998 | Naughton et al. |
| 6,200,606 B1 | 3/2001 | Peterson et al. |
| 6,530,956 B1 | 3/2003 | Mansmann |
| 6,623,733 B1 | 9/2003 | Hossainy et al. |
| 6,699,471 B2 | 3/2004 | Radice et al. |
| 6,699,484 B2 | 3/2004 | Whitmore et al. |
| 6,835,377 B2 | 12/2004 | Goldberg et al. |
| 6,872,567 B2 | 3/2005 | Thomas et al. |
| 7,229,959 B1 | 6/2007 | Drohan et al. |
| 7,905,863 B1 | 3/2011 | Forrest |
| 2002/0110544 A1 * | 8/2002 | Goldberg et al. ............ 424/93.7 |
| 2003/0050709 A1 * | 3/2003 | Noth et al. ................. 623/23.58 |
| 2003/0224411 A1 | 12/2003 | Stanton et al. |
| 2004/0078077 A1 | 4/2004 | Binette et al. |
| 2004/0136968 A1 | 7/2004 | Zheng et al. |
| 2004/0229786 A1 | 11/2004 | Attawia et al. |
| 2004/0229878 A1 | 11/2004 | DiMauro et al. |
| 2004/0235166 A1 | 11/2004 | Prockop et al. |
| 2005/0019865 A1 | 1/2005 | Kihm et al. |
| 2005/0038520 A1 | 2/2005 | Binette et al. |
| 2005/0100536 A1 | 5/2005 | Mishra |
| 2005/0118230 A1 | 6/2005 | Hill et al. |
| 2005/0205498 A1 | 9/2005 | Sowemimo-Coker et al. |
| 2005/0276792 A1 | 12/2005 | Kaminski et al. |
| 2006/0073124 A1 | 4/2006 | Garcia Castro et al. |
| 2006/0128016 A1 | 6/2006 | Tokushima et al. |
| 2006/0275273 A1 | 12/2006 | Seyedin et al. |
| 2007/0087032 A1 | 4/2007 | Change et al. |
| 2007/0122904 A1 | 5/2007 | Nordon |
| 2007/0128722 A1 | 6/2007 | Lin et al. |
| 2008/0038233 A1 | 2/2008 | Freemont et al. |
| 2009/0208464 A1 | 8/2009 | Centeno |
| 2009/0274665 A1 | 11/2009 | Akabutu et al. |
| 2010/0168022 A1 | 7/2010 | Centeno |
| 2011/0052533 A1 | 3/2011 | Centeno |
| 2011/0054929 A1 | 3/2011 | Centeno |
| 2011/0200642 A1 | 8/2011 | Centeno |
| 2011/0245804 A1 | 10/2011 | Centeno |
| 2011/0276001 A1 | 11/2011 | Centeno |
| 2013/0084341 A1 | 4/2013 | Centeno |
| 2013/0108593 A1 | 5/2013 | Centeno |

FOREIGN PATENT DOCUMENTS

| KR | 2003024028 A * | 3/2003 |
| WO | WO 97/34614 | 9/1997 |
| WO | WO 98/51317 | 11/1998 |
| WO | WO 01/80865 | 11/2001 |
| WO | WO 2004/067704 | 8/2004 |
| WO | WO 2005/046761 | 5/2005 |
| WO | WO 2005/085421 | 9/2005 |
| WO | WO 2007/087519 | 8/2007 |

(Continued)

OTHER PUBLICATIONS

Anitua et al. Autologous platelets as a source of proteins for healing and tissue regeneration. Thromb Haemost 2004; 91: 4-15.*

Roberts et al. Autologous chondrocyte implantation for cartilage repair: monitoring its success by magnetic resonance imaging and histology. Arthritis Res Ther 2003, 5:R60-R73.*

Acosta et al. 2005. The potential role of mesenchymal stem cell therapy for intervertebral disc degeneration: a critical overview. Neurosurg. Focus. vol. 19. Sep. 2005. p. 1-6.*

(Continued)

Primary Examiner — Taeyoon Kim
(74) Attorney, Agent, or Firm — Swanson & Bratschun, L.L.C.

(57) ABSTRACT

Compositions and methods are provided for the optimized expansion and implantation of mesenchymal stem cells into a patient in need thereof. Autologous mesenchymal stem cells (MSCs) to a patient in need of MSCs are harvested, expanded within novel growth parameters under the influence of autologous growth factors located on the patient's platelets.

7 Claims, 19 Drawing Sheets

(56) References Cited

FOREIGN PATENT DOCUMENTS

| WO | WO 2008/034803 | 3/2008 |
|---|---|---|
| WO | WO 2009/006161 | 1/2009 |
| WO | WO 2009/085969 | 7/2009 |
| WO | WO 2009/114785 | 9/2009 |
| WO | WO 2010/065854 | 6/2010 |
| WO | EP 2257176 | 9/2013 |

OTHER PUBLICATIONS

Hip Replacement Surgery. Johns Hopkins Medicine. downloaded on Jul. 14, 2012 from www.hopkinsmedicine.org/healthlibrary/conditions/adult/orthopaedic_disorders/hip_replacement_surgery_85,P01372. p. 1-4.*
Avascular Necrosis in patient eductation of Illinois Bone and Joint Institute. 2003 downloaded from thehipdoc.com/avas.htm. p. 1-2.*
Muller, I. et al., "Animal serum-free culture conditions for isolation and expansion of multipotent mesenchymal stromal cells from human BM" Cytotherapy (2006) 8(5):437-444.
Bernardo, M.E. et al., "Optimization of in vitro expansion of human multipotent mesenchymal stromal cells for cell-therapy approaches: further insights in the search for a fetal calf serum substitute" J. Cell. Physiol. (Apr. 2007) 211:121-130.
Acosta et al. (2005) Neurosurg Focus 19(3):E4.
Barry (2003) Novartis Found Symp. 249:86-102, 170-4,239-41.
Brisby et al. (2004) Orthop Clin. North Am. 35(1):85-89.
Buckwalter and Mankin (1998) Instr Course Lect. 47:487-504.
Caplan (1991) J Orthop Res. 9(5):641-650.
Crisostomo et al., Shock, 2006 26(6): p. 575-80.
Doucet, Ernou et al. 2005 J. Cell Physiol 205(2):228-36.
Martineau et al., Biomaterials, 2004 25(18) p. 4489-502.
Rasmusson et al., Transplantation, 2003 76(8):1208-13.
Spaggiari, Capobianco et al. 2006 Blood 107(4): 1484-90.
Ueda, Inaba et al. 2007 Stem Cells 25(6):1356-63).
Cassiede et al (1996) "Osteochondrogenic Potential of Marrow Mesenchymal Progenitor Cells Exposed to TGF-β1 or PDGF-BB as Assayed In Vivo and In Vitro" J. of Bone and Miner. Res. 11(9):1264-1273.
Kaps et al (2002) "Human Platelet Supernatant Promotes Proliferation but Not Differentiation of Articular Chondrocytes" Med. Biol. Eng. Comput. 40(4):485-490.
Ahuja, et al. (1995) Cell Immunol. 163(1):59-69, "Identification of two subpopulations of rat monocytes expressing disparate molecular forms and quantities of CD43".
Alhadlaq and Mao (2004) Stem Cells Dev 13(4):436-448, "Mesenchymal stem cells: isolation and therapeutics".
Baecher-Allan, et al. (2005) Clinical Immunology 115:10-18, "Functional analysis of highly defined, FACS-isolated populations of human regulatory CD4$^+$CD25$^+$ T cells".
Barry (2003) Novartis Found. Symp. 249:86-102, 170-4, 239-41, "Mesenchymal stem cell therapy in joint disease".
Bensaïd, et al. (2003) Biomaterials 24:2497-2502, "A biodegradable fibrin scaffold for mesenchymal stem cell transplantation".
Billard, et al. (2000) Blood 95(3):965-972, "Switch in the protein tyrosine phosphatase associated with human CD100 semaphorin at terminal B-cell differentiation stage".
Bircher, et al, (1988) Spine 13(I):98-102, "Discitis following lumbar surgery".
Borner and Follath (1989) Schweiz Med Wochenschr. 119(1):19-21, "Antibiotic therapy and long-term outcome in patients with vertebral osteomyelitis" (German, English Abstract Only).
Bühring, et al. (1999) Blood 94(7):2343-2356, "The monoclonal antibody 97A6 defines a novel surface antigen expressed on human basophils and their multipotent and unipotent progenitors".
Caligiuri, et al. (1990) J. Exp. Med. 171:1509-1526, "Functional consequences of interleukin 2 receptor expression on resting human lymphocytes. Identification of a novel natural killer cell subset with high affinity receptors".
Caplan and Bruder (2001) Trends Mol. Med. 7(6):259-264, "Mesenchymal stem cells: building blocks for molecular medicine in the 21st century".

Cashman et al. "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-beta" Blood (1990) 75(1):96-101.
Cassiede, et al. (1996) J. of Bone and Miner. Res. 11(9):1264-1273, "Osteochondrogenic potential of marrow mesenchymal progenitor cells exposed to TGF-β1 or PDGF-BB as assayed in vivo and in vitro".
Charalambous, et al. (2003) Clin. Rheumatol. 22:386-390, "Septic arthritis following intra-articular steroid injection of the knee—a survey of current practice regarding antiseptic technique used during intra-articular steroid injection of the knee".
Chazerain, et al. (1999) Rev. Rhum. Engl. Ed. 66(7-9):436-437, "Septic hip arthritis after multiple injections into the joint of hyaluronate and glucocorticoid".
Dall, et at. (1987) Clin. Orthop. Relat. Res. 224:138-146, "Postoperative discitis. Diagnosis and management".
Del Curling, et al. (1990) Neurosurgery 27(2):185-192, "Changing concepts in spinal epidural abscess: A report of 29 cases".
D'Ippolito, et al. (1999) J. Bone Miner. Res. 14(7):1115-122, "Age-related osteogenic potential of mesenchymat stromal stem cells from human verterbral hone marrow".
Elghetany and Patel (2002) Am .J. Hematol. 71:348-349, "Assessment of CD24 expression on bone marrow neutrophilic granulocytes: CD24 is a marker for the myelocytic stage of development".
Fang, et al. (2004) J. of Huazhong, Univ. of Sci. Technolog. Med. Sci. 24(3):272-274, "Biocompatibility studies on fibrin glue cultured with bone marrow mesenchymal stem cells in vitro".
Fiedler, et al. (2002) J. Cell. Biochem. 87:305-312, "BMP-2, BMP-4, and PDGF-bb stimulate chemotactic migration of primary human mesenchymal progenitor cells".
Fiedler, et al. (2004) J. Cell. Biochem. 93:990-998, "To go or not to go: Migration of human mesenchymal progenitor cells stimulated by isoforms of PDGF".
Fortier, et al. (1998) Am. J. Vet. Res, 59(9):1182-1187, "Isolation and chondrocytic differentiation of equine bone marrow-derived mesenchymal stem cells".
Fujiwara, et al. (1994) Neurol. Med. Chir. (Tokyo) 34(6):382-384, "Acute purulent discitis with epidural abscess of the cervical spine in an adult".
Gazzit, et al. (1995) Blood 86(1):381-389, "Purified CD34$^+$ Lin$^-$ Thy$^+$ stem cells do not contain clonal myeloma cells".
Gibson and Waddell (2005) Spine 30(20):2312-2320 "Surgery for degenerative lumbar spondylosis: updated cochrane review".
Graber and Hanley (2003) Spine 28(2):186-193, "Recent advances in disc cell biology".
Gruber, et al. (2004) Platelets 15(1):29-35, "Platelet-released supernatants increase migration and proliferation, and decrease osteogenic differentiation of bone marrow-derived mesenchymal progenitor cells under in vitro conditions".
Gustafson, et al. (1989) Am. J. Vet. Res. 50(12):2018-2022, "Further investigations into the potentiation of infection by intra-articular injection of polysulfated glycosaminoglycan and the effect of filtration and intra-articular injection of amikacin".
Hickstein, et al., (1992) Proc. Natl. Acad. Sci. U.S.A 89(6):2105-2109, "Identification of the Promoter of the Myelomonocytic Leukocyte Integrin CD11b".
Hirschi et al., (1999) Circ. Res. 84(3):298-305, "Endothelial Cells Modulate the Proliferation of Mural Cell Precursors Via Platelet-Derived Growth Factor-BB and Heterotypic Cell Contact".
Hoelscher, et al. (2000) Spine 25(15):1871-1877, "Effects of very high antibiotic concentrations on human intervertebral disc cell proliferation, viability, and metabolism in vitro".
Huang arid Terstappen, (1994) Nature 368(6472):664, "Formation of Haematopoietic Microenvironment and Haematopoietic Stem Celts from Single Human Bone Marrow Stem Cells".
Huss (2000) J. Hematother. Stem Cell Res. 9:783-793, "Perspectives on the morphology and biology of CD34-negative stem cells".
Iversen, et al. (1992) Acta Orthop. Scand. 63(3):305-309, "Prognosis in postoperative discitis, A retrospective study of 111 cases".

(56) References Cited

OTHER PUBLICATIONS

Johnstone and Yoo (1999) Clin. Orthop. Relat. Res. 367 Suppl:S156-162, "Autologous mesenchymal progenitor cells in articular cartilage repair".
Kambin and Schaffer (1989) Clint Orthop. Relat. Res, 238:24-34, "Percutaneous lumbar discectomy Review of 100 patients and current practice".
Kang, et al. (2005) J. Cell. Biochem. 95:1135-1145, "Role of c-Jun N-terminal kinase in the PDGF-induced proliferation and migration of human adipose tissue-derived mesenchymal stem cells".
Katz, et al. (1987) Leuk. Res. 11(4):339-344, "Effect of platelet-derived growth factor on enriched populations of haemopoietic progenitors from patients with chronic myeloid leukaemia".
Kilian, et al. (2004) Eur. J. Med. Res. 9(7):337-344, "Effects of platelet growth factors on human mesenchymal stem cells and human endothelial cells in vitro".
Kirshenbaum, et al. (1999) Blood 94:2333-2342, "Demonstration that human mast cells arise from a progenitor cell population that is CD34+, c-kit+, and expresses aminopeptidase N (CD13)".
Kitoh, et al. (2004) Bone 35:892-898, "Transplantation of marrow-derived mesenchymal stem cells and platelet-rich plasma during distraction osteogenesis—a preliminary result of three cases".
Koh, et al. (2005) Biochem. Biophys. Res. Commun. 329:1039-1045, "Co-culture of human CD34+ cells with mesenchymal stem cells increases the survival of CD34+ cells against the 5-aza-deoxycytidine- or trichostatin A-induced cell death".
Kortelainen and Särkioja (1990) Z Rechtsmed. 103:547-554, "Fatal complications of intramuscular and intra-articular injections".
Laiho and Kotilainen (2001) Joint Bone Spine 68:443-444, "Septic arthritis due to *Prevotella bivia* after intra-articular hip joint injection".
Luyten (2004) Curr. Opin. Rheumatol. 16:599-603, "Mesenchymal stein cells in osteoarthritis".
Magne, et al. (2005) Trends Mol. Med. 11(11):519-526, "Mesenchymal stem cell therapy to rebuild cartilage".
Medina et al., (2000) Cytometry 39(3):231-234, "Purification of Human Tonsil Plasma Cells: Pre-Enrichment Step by Immunomagnetic Selection of CD31(+) Cells".
Miyata, et al. (2005) J. Cell. Physiol. 204:948-955, "Platelet-derived growth factor-BB (PDGF-BB) induces differentiation of bone marrow endothelial progenitor cell-derived cell line TR-BME2 into mural cells, and changes the phenotype".
Morshed, et al. (2004) J. Bone Joint Surg. Am. 86:823-826, "Septic arthritis of the hip and intrapelvic abscess following intra-articular injection of hylan G-F 20. A case report".
Murphy, et al. (2003) Arthritis Rheum. 48(12):3464-3474, "Stem cell therapy in a caprine model of osteoarthritis".
Murray, et al. (1999) Exp. Hematol. 27:1282-1294, "CD109 is expressed on a subpopulation of CD34+ cells enriched in hematopoietic stem and progenitor cells".
Nielsen, et al. (1990) Acta Radiol. 31(6):559-563, "Postoperative discitis. Radiology of progress and healing".
Olweus et al., (1995) Blood 85(9):2402-2413, "CD64/Fc Gamma RI is a Granulo-Monocytic Lineage Marker on CD34+ Hematopoietic Progenitor Cells".
Onofrio (1980) Clin. Neurosurg. 27:481-516, "Intervertebral discitis: incidence, diagnosis, and management".
Ordog et al., "Purification of interstitial Cells of Cajal by Fluorescence-Activated Cell Sorting" Am. J. Physiol, Cell Physiol (2004) 286(2):448-456.
Orpen and Birch (2003) J. Spinal Disord. Tech. 16(3):285-287, "Delayed presentation of septic arthritis of a lumbar facet joint after diagnostic facet joint injection".
Oshima, et al. (2004) OsteoArthritis Cartilage 12:811-817, "Fate of transplanted bone-marrow-derived mesenchymal cells during osteochondral repair using transgenic rats to simulate autologous transplantation".

Otawa, et al. (2000) Leukemia Research 24:359-366, "Comparative multi-color flow cytometric analysis of cell surface antigens in bone marrow hematopoietic progenitors between refractory anemia and aplastic anemia".
Park, et al. (2005) Artif. Organs 29(10);838-860, "Tissue-engineered cartilage using fibrin/hyaluronan composite gel and its in vivo implantation".
Pellaton, et at. (1981) Schweiz. Rudnsch. Med. Prax. 70(52);2364-2367, "Spectic arthritis following repeated intraarticular injections of glycosaminoglycanpolysulfat (Arteparon®) and steroids for osteoarthrosis of the knee joint" (French, English Abstract Only).
Pietramaggiori, et al. (2006) Wound Rep. Reg. 14:573-580, "Freeze-derived platelet-rich plasma shows beneficial heating properties in chronic wounds".
Ponte and McDonald (1992) J. Fam. Pract. 34(6):767-771, "Septic discitis resulting from *Escherichia coli* urospesis".
Reddi and Cunningham (1990) Biomaterials 111:33-34, "Bone induction by osteogenin and bone morphogenetic proteins".
Richardson, et al., (2006) Stem Cells 24:707-716, "Intervertebral disc cell-mediated mesenchymal stem cell differentiation".
Ruszymah (2004) Med. J. Malaysia 59 Suppl.B:30-1, "Autologous human fibrin as the biomaterial for tissue engineering".
Sah, et al. "Effects of fibrin glue components on chondrocyte growth and matrix formation," in 49th Annual Meeting of the Orthopaedic Research Society, poster #0721.
Sanchez, et al, (2003) Int. J. Oral Maxiliofac. Implants 18:93-103, "Is platelet-rich plasma the perfect enhancement factor? A current review".
Sato et al., (1999) Blood 94(8):2548-2554, "Reversible Expression of CD34 by Murine Hematopoietic stem cells".
Silverman, et al. (Jun. 1999) Plast. Reconstr. Surg. 103(7):1809-1818, "Injectable tissue-engineered cartilage using a fibrin glue polymer".
Singer, et al (1984) Leuk, Res. 8(4):535-545, "Evidence for a stem cell common to hematopoiesis and its in vitro microenvironment: studies of patients with clonal hematopoietic neoplasia".
Singer et al., (1987) Blood 70(2):464-474, "Simian Virus 40-Transformed Adherent Cells From Human Long-Term Marrow Cultures: Cloned Cell Lines Produce Cells with Stromal and Hematopoietic Characteristics".
Simmons and Torok-Storb, (1991) Blood 78(11):2848-2853, "CD34 Expression by Stromal Precursors in Normal Human Adult Bone Marrow".
Stacey, et al. (2000) Eur. J. Vasc. Endovasc. Surg. 20:296-301, "Randomised double-blind placebo controlled trial of topical autologous platelet lysate in venous ulcer healing".
Terstappen et al., (1991) Blood 77(6):1218-1227, "Sequential Generations of Hematopoietic Colonies Derived From Single Nonlineage-Committed CD34+CD38–Progenitor Cells".
Toba et al., (1999) Cytometry 35(3):249-259, "Novel Technique for the Direct Flow Cytofluorometric Analysis of Human Basophils in Unseparated Blood and Bone Marrow, and the Characterization of Phenotype and Peroxidase of Human Basophils".
Weber (1988) Z. Orthop Ihre Grenzeb 126(5):555-562, "Infectious damage to the intervertebral disk-before and following discotomy" (German, English Abstract Only).
Willems, et al. (Jun. 2004) J. Spinal Disord. Tech. 17(3):243-247, "Lumbar discography: should we use prophylactic antibiotics? A study of 435 consecutive discograms and a systematic review of the literature".
Willheim, et al. (1995) J. Immunological Methods 182:115-129, "Purification of human basophils and mast cells by multistep seperation technique and mAb to CDw17 and CD117/c-kit".
Xaymardan et al., (2004) Circ Res. 94(5):E39-E45, "Platelet-Derived Growth Factor-AB Promotes the Generation of Adult Bone Marrow-Derived Cardiac Myocytes".
Yamada, et al. (2003) J. Cranio-Maxillofac. Surg. 31:27-33, "Bone regeneration following injection of mesenchyrnal stem cells and fibrin glue with a biodegradable scaffold".
Zhu, et al. (2006) Stem Cells 24:416-425, "Hypoxia and serum deprivation-induced apoptosis in mesenchymal stem cells".

(56) References Cited

OTHER PUBLICATIONS

Ando et al (2007) "Cartilage repair using an in vitro generated scaffold-free tissue-engineered construct derived from porcine synovial mesenchymal stem cells" Biomaterials 1-9. Available Website: www.sciencedirect.com.
Castro et al (2002) "Failure of Bone Marrow Cells to Transdifferentiate into Neutral Cells In Vivo" Science 297:1299.
Centeno et al (2008) "Regeneration of meniscus cartilage in a knee treated with percutaneously implanted autologous mesenchymal stem cells" Medical Hypotheses 71:900-908.
Centeno and Faulkner (2012) "The Use of Mesenchymal Stem Cells in Orthopedics" Stem Cells and Cancer Stem Cells 1:173-179.
Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Adherent Technique).
Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Novel Technique).
Mezey et al and Castro et al (2003) "Comment on and Response to Comment on Failure of Bone Marrow Cells to Transdifferentiate into Neutral Cells In Vivo" Science 299:1184b-1184c.
Tosh et al (2002) "Conversion of Pancreatic Cells to Hepatocytes" Biochem. Soc. Trans. 30:51-55.
Centeno et al (2006) "Partial Regeneration of the Human Hip Nucleated Cell Transfer: A Case Study" Pain Physician 9:253-256.
Deschaseaux et al (2003) "Direct Selection of Human Bone Marrow Mesenchymal Stem Cells Using an Anti-CD49a Antibody Reveals Their $CD45^{med,low}$ Phenotype" British Journal of Haematology 122:506-517.
Fraser et al (1993) "Each Hypersensitive Site of the Human Beta-Globin Locus Control Region Confers a Different Developmental Pattern of Expression on the Globin Genes" Genes & Development 7:106-113.
Munirah et al (2008) "Autologous Versus Pooled Human Serum for Articular Chondrocyte Growth" Journal of Orthopedic Surgery 16(2):220-229.
Nakayama et al (2000) "Evaluation of Glycosaminoglycans Levels in Normal Joint Fluid of the Knee" J. Nippon Med. Sch. 67(2)92-95.
Rolf et al (1999) "Intra-Articular Absorption and Distribution of Ketoprofen After Topical Plaster Application and Oral Intake in 100 Patients Undergoing Knee Arthroscopy" Rheumatology 38:564-567.
Tondreau et al (2004) "Isolation of BM Mesenchymal Stem Cells by Plastic Adhesion or Negative Selection: Phenotype, Proliferation Kinetics and Differentiation Potential" Cyrotherapy 6(4):372-379.
Gajdusek et al (1993) "Basic Fibroblast Growth Factor and Transforming Growth Factor Beta-1: Synergistic Mediators of Angiogenesis In Vitro" J. Cell. Physiol. 157(1):133-144.
Luis A. Solchaga et al (2002) "Treatment of Osteochondral Defects with Autologous Bone Marrow in a Hyaluronan-Based Delivery Vehicle", Tissue Engineering, vol. 8, No. 2, pp. 333-347.
Prins et al (1982) "Effect of Purified Growth Factors on Rabbit Articular Chondrocytes in Monolayer Culture. II. Sulfated Proteoglycan Synthesis" Arthritis & Rheumatism, 25(10):1228-1238.
Yang et al (1994) "Cardioprotective Effects of Platelets Against Ischaemia-Reperfusion Injury are Related in Part to Platelet Glutathione Redox Cycle" Cardiovasc. Res. 28(10):1586-1593 Abstract.
Ye et al (2007) "Effect of Three Growth Factors on Proliferation and Cell Phenotype of Human Fetal Meniscal Cells" Chinese Journal Reconstructive Surgery 21(10):1137-1138 with English Abstract.
Sun et al (2001) "Recombinant Human Acidic Fibroblast Growth Factor Accelerates the Healing of Full-Thickness Dermal Wounds in Pigs" Modern Rehabilitation 5(9):31 with English Abstract.
Lange et al (2007) "Accelerated and Safe Expansion of Human Mesenchymal Stromal Cells in Animal Serum-Free Medium for Transplantation and Regenerative Medicine" Journal of Cellular Physiology 213(1):18-26.
Schallmoser et al (2007) "Human Platelet Lysate Can Replace Fetal Bovine Serum for Clinical-Scale Expansion of Functional Mesenchymal Stromal Cells" Transfusion 47(8):1436-1446.
Centento et al. (2008) The American Journal of Case Reports 9:201-206 "Increased Knee Cartilage Volume in Degenerative Joint Disease using Percutaneously Implanted, Autologous Mesenchymal Stem Cells, Platelet Lysate and Dexamethasone".
Centeno et al. (2008) Pain Physician 11(3):343-353 "Increased Knee Cartilage Volume in Degenerative Joint Disease using Percutaneously Implanted, Autologous Mesenchymal Stem Cells".
Centeno et al. (2011) Bioengineering & Biomedical Science S2:007 "A Case Series of Percutaneous Treatment of Non-Union Fractures with Aulogous, Culture Expanded, Bone Marrow Derived, Mesenchymal Stem Cells and Platelet Lysate".
Xian and Foster (2006) Current Stem Cells Research and Therapy 1:213-229 "Repair of Injured Articular and Growth Plate Cartilage Using Mesenchymal Stem Cells and Chondrogenic Gene Therapy".
Kravitz et al. "How Do Muscles Grow", IDEA Fitness Journal; 3(2), 23-25 (2006) (http://www.unm.edu/kravitz/Article%20folder/musclesgrowLK.html).
Regenexx™ PR article published Nov. 8, 2007; downloaded May 14, 2012.
Ries et al. (2007) Blood 109(9):4055-4063 "MMP-2, MT1-MMP, and TIMP-2 are essential for the invasive capacity of human mesenchymal stem cells: differential regulation by inflammatory cytokines".

\* cited by examiner

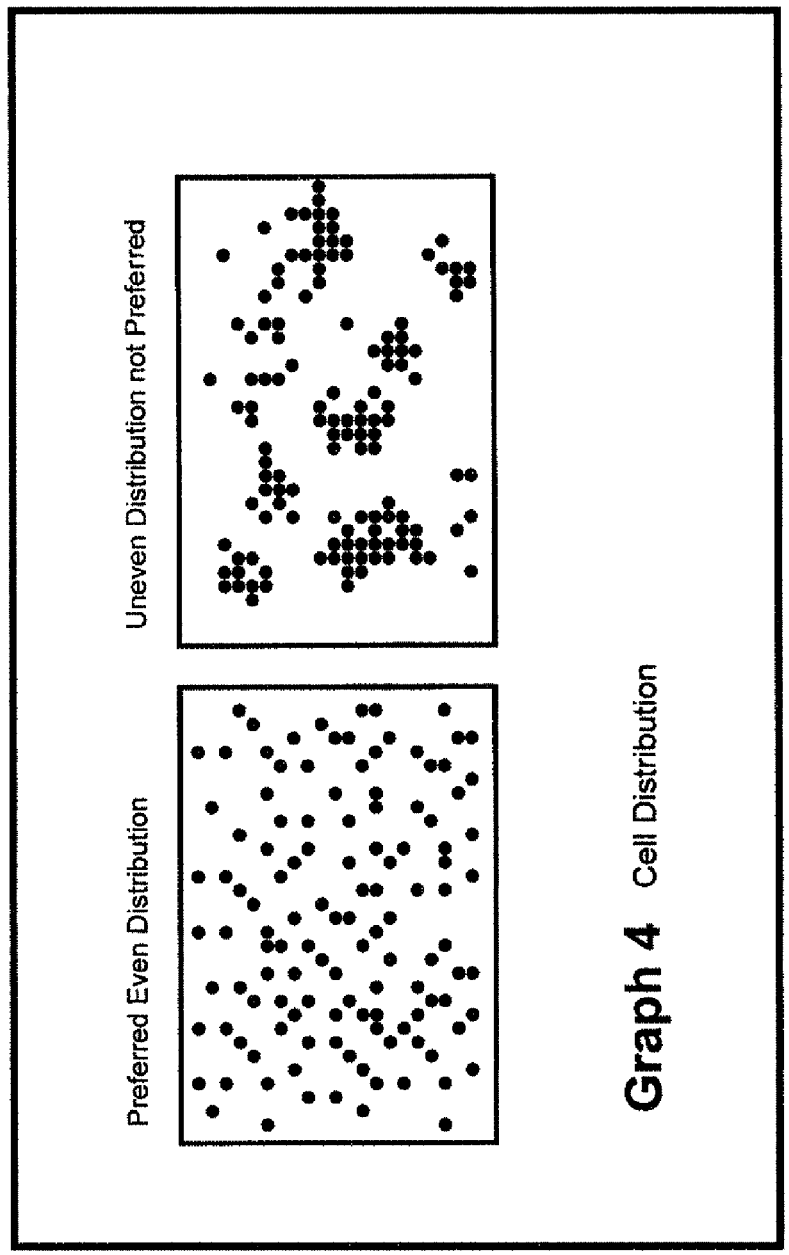

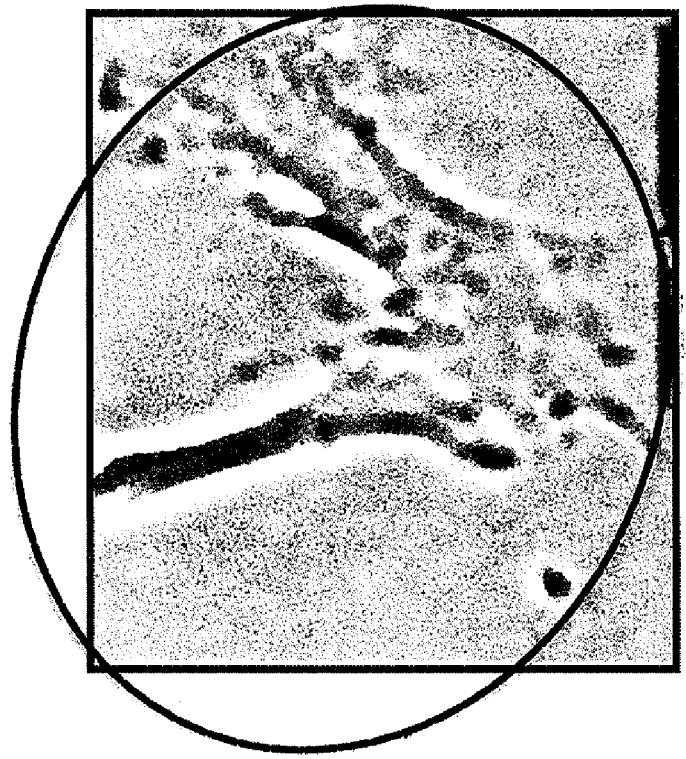
Fig. 1E-TYPE II
Fig. 1E-TYPE I

Fig. 1E-TYPE IV
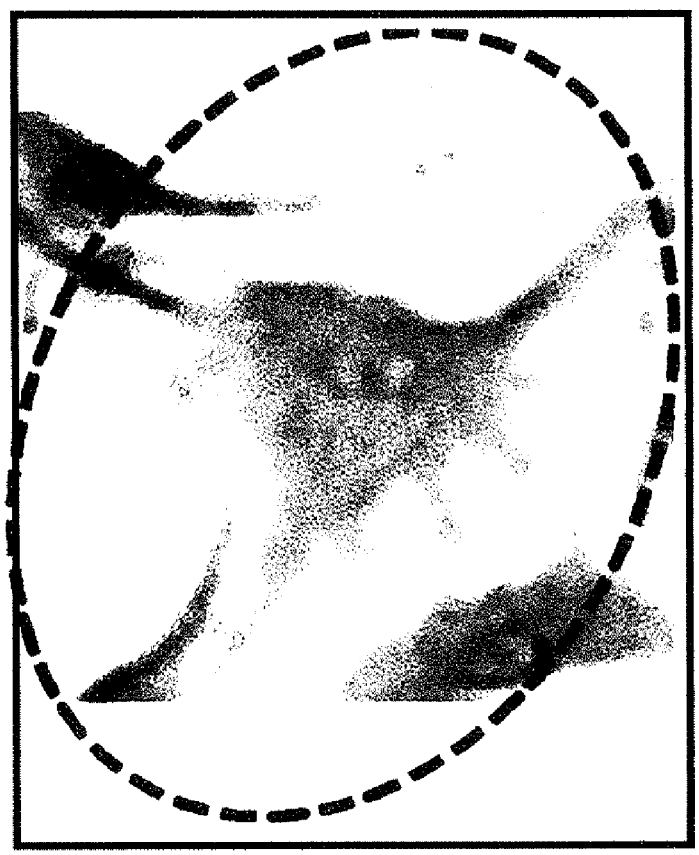
Fig. 1E-TYPE III

METHODS AND COMPOSITIONS FOR OPTIMIZED EXPANSION AND IMPLANTATION OF MESENCHYMAL STEM CELLS

TECHNICAL FIELD

The invention generally relates to compositions and methods for isolation, expansion and implantation of stem cells into a host in need thereof. More specifically, the invention relates to the replacement and repair of target tissue using autologous mesenchymal stem cells (MSCs) expanded under optimized growth conditions.

BACKGROUND OF THE INVENTION

Mesenchymal stem cells are pluripotent blast or embryonic-like cells located in blood, bone marrow, dermis and periosteum. In general these cells are capable of renewing themselves over extended periods of time as well as, under various environmental conditions, differentiating into cartilage, bone and other connective tissue. Recently, various investigators have researched the potential for using these cells to repair or regenerate target tissues, e.g., bone, cartilage, etc. In this manner MSCs have been reported to have regenerative capabilities in a number of animal models. See Acosta et al. (2005) Neurosurg Focus 19(3):E4; Barry (2003) Novartis Found Symp. 249:86-102, 170-4, 239-41; Brisby et al. (2004) Orthop Clin. North Am. 35(1):85-89; Buckwalter and Mankin (1998) Instr Course Lect. 47:487-504; Caplan (1991) J Orthop Res. 9(5):641-650. Further, these finding are being extended in clinical trials to humans, however, most of these trials require in vitro expansion of isolated, non-autologous MSCs using highly concentrated recombinant cytokines and growth factors. For example, most human studies have utilized isolated MSCs from bone marrow (or peripheral blood), followed by ex-vivo expansion of the cells in a laboratory setting using a fetal bovine serum (FBS) based culture medium spiked with various recombinant growth factors. These supplemented FBS-based culture mediums have shown the capacity to support MSC expansion but also include the risk of cross-contamination of infectious vectors, use of non-Food and Drug Administration (FDA) approved drugs/factors, e.g., recombinant TGF-$\beta$, FGF, cross species reactions, and possible increased potential for forming cancerous progenitors.

In addition, most of the MSC-based human studies have required trained laboratory staff and laboratory equipment to perform the expansion of the isolated MSCs. These techniques are not amenable to performance by physicians and/or hospital staff, especially given that physicians are legally bound by FDA protocols and procedures concerning non-FDA approved drugs. Therefore, it is difficult for MSC based therapies to be performed in a pragmatic manner, i.e., in a hospital setting with hospital employees. Given these numerous concerns, most MSC based research is directed at non-autologous cells that have been isolated and cultured into permanent cell lines.

Doucet (Doucet, Ernou et al. 2005 J. Cell Physiol 205(2): 288-36) has recently described a technique for expanding MSCs of young healthy donors using a 5% platelet lystate enriched culture medium. However, Doucet's investigations did not determine effectiveness of these procedures on elderly patients, patients with degenerative joint diseases (for example osteoarthritis), or other patient specific characteristics. Nor was the study performed using any expansion conditions except for 5% platelet lysate enriched culture medium. In this light, it has been shown that there is a wide variation in MSC growth in patients with and without osteoarthritis, with age, with gender, and based on certain genetic phenotypes. Therefore the Doucet study has very limited applicability to real life situations, where most patients in need of MSC-based therapy are generally either older, or have degenerative joint, organ, or spinal diseases. The Doucet data also does not apply to other disease states of bony metabolism such as avascular necrosis or osteonecrosis. In addition, the generalized findings in Doucet are not gender or age specific, having little guidance on how to treat the different sexes or how to expand MSC's from patients of advanced age.

MSC's can readily differentiate in culture depending on cytokine exposure, environmental conditions (pressure, attachment opportunities, passage treatment, etc. . . . ), or other chemical exposure. For example, exposure to varying levels of TGF-beta, FGF, and/or PDGF can all have impacts on the final cell phenotype produced in culture. In addition, leaving cells in culture longer has impacts on differentiation potential. Cells can be cultured for a certain visual morphology, confluence, or density, all of which impacts the final cell product produced and its potential for certain types of tissue repair. As a result, this invention focuses on controlling factors/parameters so as to produce a homogeneous cell product with certain restorative properties.

In replacing or repairing tissue with MSC's, one concern is the use of non-autologous cells. While MSC's have been traditionally considered immune privileged, recent investigations have demonstrated their activation of the natural killer cell system in a foreign host. (Spaggiari, Capobianco et al. 2006 Blood 107(4): 1484-90) This makes the use of non-autologous cells difficult, as it is anticipated that the host's immune system will attack these foreign cells and potentially decimate the population of transplanted MSCs, thus severely limiting their repair capabilities. In addition, a recent work published by Ueda may have other far reaching implications for the use of non-autologous cells. (Ueda, Inaba et al. 2007 Stem Cells 25(6):1356-63) This study demonstrated that senile mice with osteoporosis transferred that disease into normal mice through a bone marrow vector. This suggests that the MSC's of the senile mice with osteoporosis once transferred to normal healthy mice were able to transfer that disease state into normal healthy mice. This genetic vector for disease transmission is concerning, as any donor MSC's would theoretically need to be screened for all known genetic susceptibilities and diseases that may be transferred by the donor.

There is a need in the art for MSC expansion techniques that do not use drugs or growth factors which are not FDA approved and can be effectively used to replace tissue in a patient in need thereof. This replacement should be with autologous cells that have been optimally expanded based on the patient's medical condition, age, gender and other relevant replacement conditions. In addition, there is a need for autologous techniques to yield a homogeneous cell line with known regeneration capabilities and rigid quality control.

The present invention is directed toward overcoming one or more of the problems discussed above.

SUMMARY OF THE INVENTION

Embodiments of the invention provide compositions and methods for ex-vivo expansion of autologous human mesenchymal stem cells (MSCs) and subsequent implantation into target patients in need thereof. These MSCs are optimized for their capacity to implant and replace/regenerate target tissue, e.g., regenerate cartilage in a knee joint. As discussed above, they are also optimized to produce a homogeneous cell line with rigid quality control which expresses one or more of the following cell surface antigens: CD29, CD44, CD59, CD73, CD90, CD166, and CD105 and in some embodiments express two, three, four, five, six or seven of the above cell surface antigens. In addition, some optimized cells described herein do not express one or more of the following cell surface antigens: CD14, CD31, CD45, and/or CD106.

Aspects of the invention include novel expansion compositions that do not require purified or recombinant growth factors, cytokines, or non-naturally occurring human factors. In particular, expansion compositions are designed to include varying amounts (and varying timing) of the introduction of platelet lysate to optimize cell growth, especially optimize cell growth for cells at time of implantation into a target patient. Optimization in some instances includes expanding cells in a controlled manner to facilitate the cells capability of successfully implanting in a patient in need thereof; in some cases cell growth and cell growth conditions are monitored and modified to keep the cells within a predetermined "growth channel", i.e., expansion of cells to a required number prior to a limited number of cell passages. These platelet lysate based growth conditions provide for consistent and autologous release of the necessary factors for facilitating ex-vivo MSC expansion within this growth channel. In addition, in order to ensure homogeneity and strict quality controls, the "growth channel" has multiple other embodiments such as cell density, morphology, and culture pattern. Again, these are designed to produce a consistent cell expansion with known cell reparative properties, as small changes to this formula for cell growth will result in a wholly different cell product with different differentiation and repair properties.

Aspects of the invention also include preparing a patient for receipt of optimally cultured MSCs by implanting the cells with determined amounts of platelets or platelet lysate. Implantation of cells and platelets can occur simultaneously or subsequent to each other. In typical embodiments the MSCs and platelets and platelet lysate are from the patient into which the MSCs and platelets/platelet lysate will be implanted.

Aspects of the invention also include a method for isolation of MSC's from a patient in need of MSC-based restoration therapy, optimized expansion of these isolated MSCs using cell specific expansion data obtained using varying amounts of platelet lysate and culture decisions based on cell properties (such as confluence, morphology, cell culture pattern, etc. . . . ) necessary to ensure proper and homogeneous growth for a target need (i.e., growth in the growth channel), and implantation of the expanded cells with our without context dependent MSC growth facilitator materials.

Aspects of the invention are particularly useful where cells are harvested and replaced into patients having osteoarthritis or other diseases of cartilage or bone metabolism (such as avascular necrosis or osteoporosis) given that the cells harvested from these patients conventionally show little prospect of use in replacement therapy. However, this statement is not meant to limit the scope or use of this invention to one application.

Aspects of the invention also provide a growth channel for ensuring that harvested MSCs are maintained in a natural manner that facilitates cell implantation back into the patient. These cells are autologous and optimized for potential growth in the target using only natural factors from the same host that the cells were harvested from, i.e., no synthetic or recombinant factors used to facilitate cell growth. In typical growth channel embodiments the cells are expanded and ready for implementation before their $10^{th}$ passage and in other embodiments the cells are expanded and ready for implementation by their 3rd, $4^{th}$, $5^{th}$, $6^{th}$, $7^{th}$, $8^{th}$ or $9^{th}$ passage (post harvest). Cells that are implanted after about the $10^{th}$ passage show an increasing tendency to be ineffective for clinical use.

Aspects of the invention provide for ensuring that expanded MSCs are within a growth channel by manually counting the cells. In other aspects of the invention MSCs are visually inspected for characteristic indication that the cells are within the growth channel, proper indicators include culture morphology, culture pattern and culture density. In some aspects both the number of cells and the visual inspection of cells are used to indicate whether cells are within a growth channel of the invention. Note that visual inspection can be performed on site of the cultured MSCs, e.g., a blood bank in a hospital that has been contracted to expand the cells, or via a remote site, where experienced tissue culture personnel view cultures via digital camera microscopy (live video or updated pictures or other like technology) and provide feedback to distant personnel on-site regarding conditions of cultured cells.

Finally, aspects of the invention provide cell populations that are enriched for identified phenotypes using the methods described herein, the phenotype including one or more of the following cell surface antigens: CD29, CD44, CD59, CD90, CD166, CD73 and CD105. Cells identified herein further are typically negative for the CD14, CD31, CD45 and CD106 cell surface antigens. In some embodiments the optimized and expanded cell populations express CD29 and CD44 with at least one other of the following cell surface antigens: CD59, CD90, CD105, and CD66. Therefore, in some embodiments the optimized cell populations of the invention express at least: CD29, CD44 and CD59; express CD29, CD44 and CD90; express CD29, CD44 and CD105 or express CD29, CD44 and CD66.

Cells prepared using the methods described herein having the above described phenotype show optimal growth characteristics for implantation into a patient in need thereof.

These and various other features and advantages of the invention will be apparent from a reading of the following detailed description and a review of the appended claims.

BRIEF DESCRIPTION OF THE DRAWINGS

FIG. 1A-E shows various illustrative aspects of the "Growth Channel" herein described including Cell Growth Rate, Cell Density, Cell Morphology, and Cell Culture Pattern. A: Cell Growth Rate to Optimize Expansion for Repair. Doubling time is defined as the number of days to double the count of cells in monolayer culture. This is a key metric, as cells which are capable of repair are readily able to exponentially grow in culture. The % platelet lysate required to allow doubling time within the acceptable growth channel also determines the amount of platelet lysate that will be needed to support cell expansion and engraftment in-vivo. Cell Culture Actions:

Figure 1A:
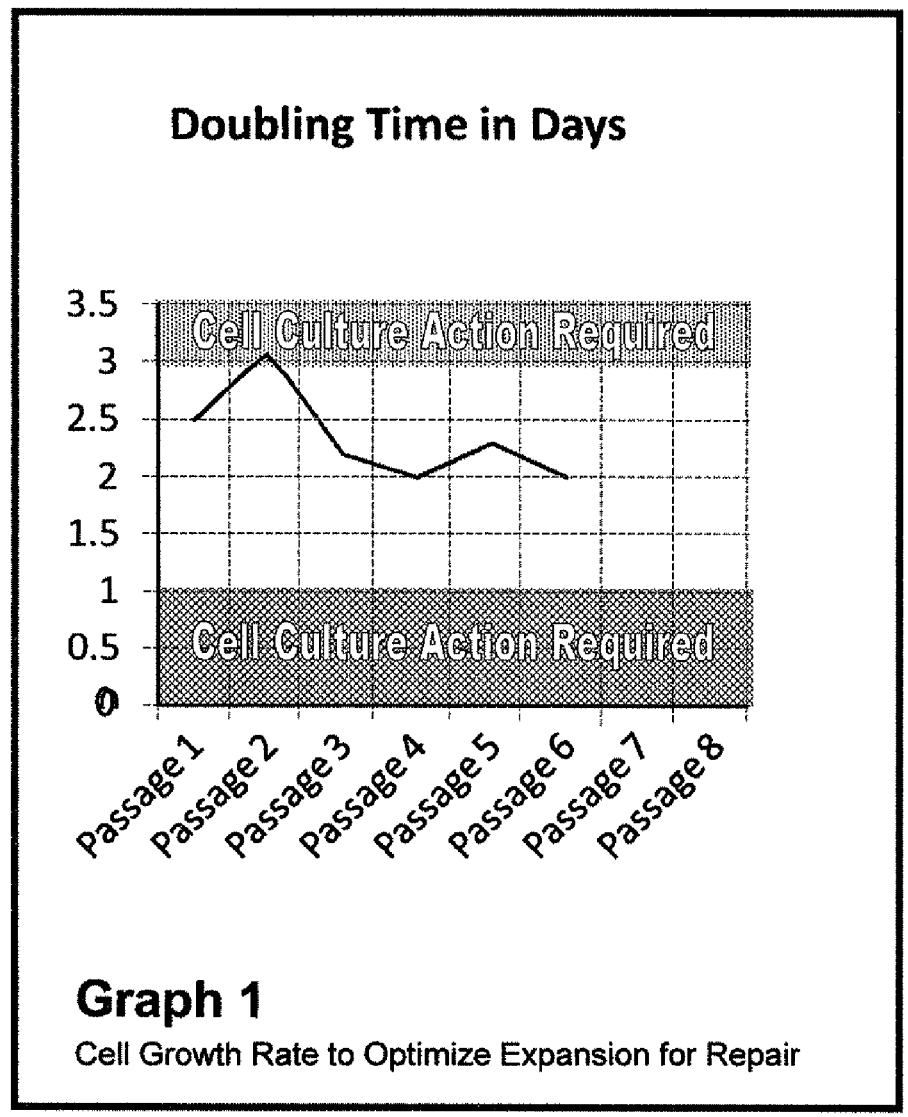

Above expected channel (>3 days): Increase platelet lysate concentration until growth rate is in the expected channel; Reseed at higher density until growth rate is in the expected channel;

Below expected channel (<1 day): Decrease platelet lysate concentration until growth rate is in the expected channel; Reseed at lower density until growth rate is in the expected channel.

B: Exemplar of two 10 cc marrow draws at the PSIS yielding >100 nucleated cells into colony formation culture and approximately 700,000 MSC's out of colony formation culture (after 7-10 days in 20% lysate). In this example, the growth channel is shown in that any lag of doubling time results in a cell culture action as already described. Cell Culture Action:

Above expected channel as shown: Increase platelet lysate concentration until growth rate is in the expected channel; Reseed at higher density until growth rate is in the expected channel;

Below expected channel as shown: Decrease platelet lysate concentration until growth rate is in the expected channel; Reseed at lower density until growth rate is in the expected channel.

C: Cell Confluence is defined as the percentage of free space between cells in monolayer culture. As shown here, cells that are too tightly packed will quickly move toward a differentiated state, while cells that are too loosely packed will fail to hit growth rate targets. Spatial distribution of cells can be quantified by the following equation: Surface area*(% Confluence)/Cell number. This figure should be in the range of 18-23. Cell Culture Actions:

Below expected channel (<18): Decrease platelet lysate concentration until confluence is in the expected channel; Reseed at lower density until confluence is in the expected channel;

Above expected channel (>23): Reseed at higher density until confluence is in the expected channel (from $12 \times 10^3$ cells/cm$^2$ to $15 \times 10^3$ cells/cm$^2$);

Significantly above expected channel (>27); Increase platelet lysate concentration.

D: Cell Distribution is defined as the randomness of cells in two dimensional space (monolayer culture), Randomly distributed cells are within the growth channel, clumped or unevenly distributed cells are out of the growth channel. Cell Culture Actions:

Out of expected channel (unevenly distributed): Reseed at higher density until evenly distributed; Passage cells sooner than expected.

E: MSC Morphology type associated with this invention and types not associated. MSC's can be grown with various environmental stimuli and conditions to prefer one phenotype over another. Displayed here are phenotypes not associated with this invention. The phenotype associated with this invention is spindle shaped. Or type 1 as shown. Any deviation from this morphology requires a cell culture action as described.

TYPE 1: Photomicrograph of Type 1 MSC at 10× taken from the iMSC's grown according to the growth channel considerations described in this invention.

TYPE II: Photomicrograph of Type II MSC at 10× taken from: Human mesenchymal stem cells in contact with their environment: surface characteristics and the integrin system Denitsa Docheva *, Cvetan Popov, Wolf Mutschler, Matthias Schieker J. Cell Mol. Med. Vol 11, No 1, 2007 pp. 21-38.

TYPE III: Photomicrograph of Type III MSC at 20× taken from: Hepatogenic differentiation of human mesenchymal stem cells from adipose tissue in comparison with bone marrow mesenchymal stem cells Raquel Talens-Visconti, Ana Bonora, Ramiro Jover, Vincente Mirabet, Francisco Carbonell, Jose Vincente Castell, Maria Jose Gomez-Dechon *World J. Gastroenterol* 2006 September 28; 12(36): 5834-5845.

TYPE IV: Photomicrograph of Type IV MSC at 10× taken from: Autologous Bone Marrow-Derived Cultured Mesenchymal Stem Cells Delivered in a Fibrin Spray Accelerate Healing in Murine and Human Cutaneous Wounds, V FALANGA, S IWAMOTO, M CHARTER, T YUFIT, J BUTMARC, N KOUTTAB, D SHRAYER, P; CARSON TISSUE ENGINEERING Volume 13, Number 6, 2007.

Cell Culture Actions:

Out of expected channel (>30% Type II cells): Increase platelet lysate concentration until morphology is type I or transplant if passage >5;

Significantly out of expected channel (>30% Type III of IV cells); Passage or transplant cells sooner than expected; Cells may not have desired effect.

Figure 2:
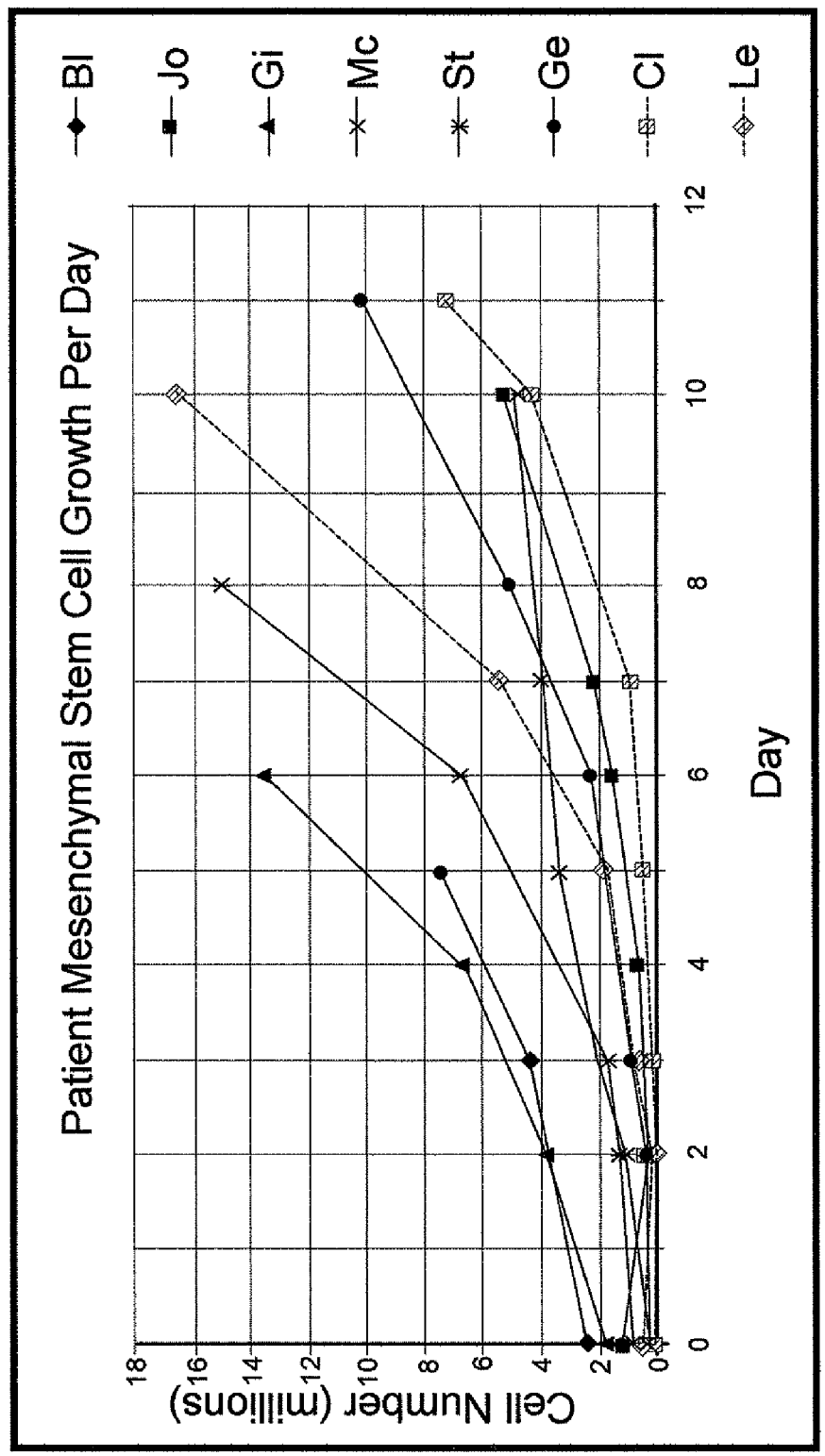
Figure 3A:
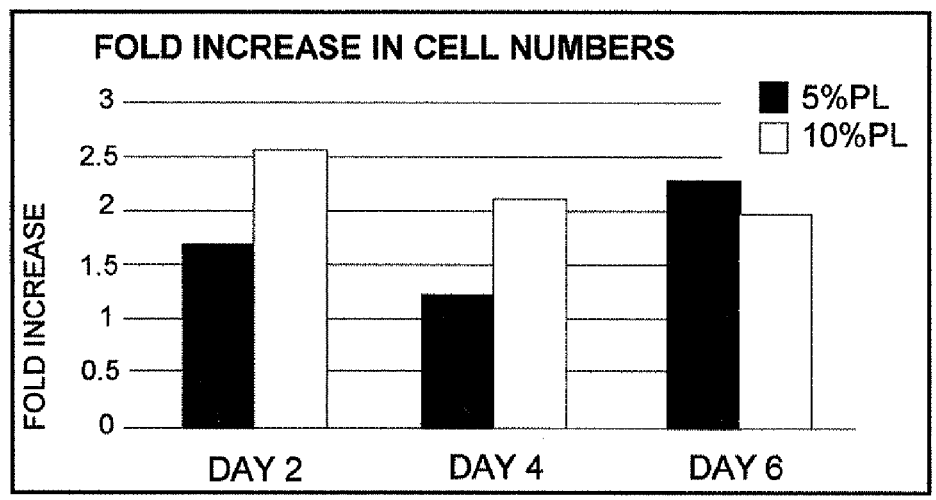
Figure 3B:
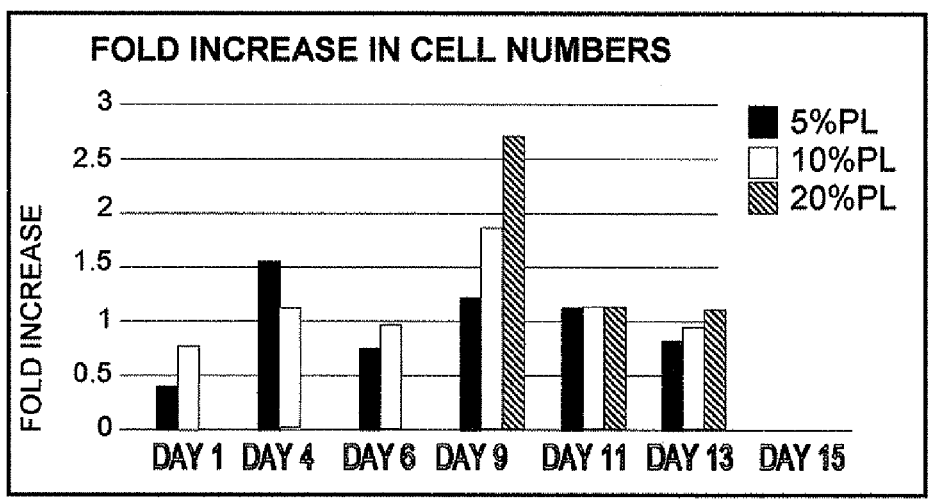
Figure 3C:
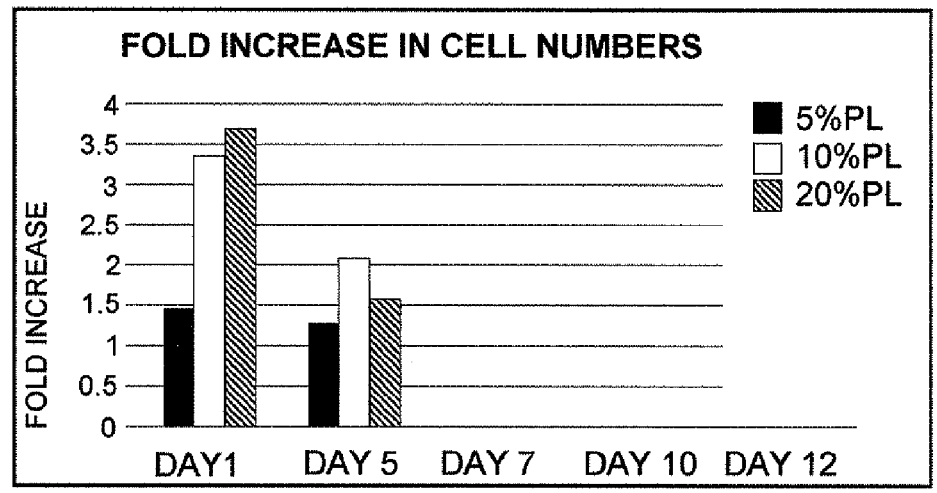
Figure 3D:
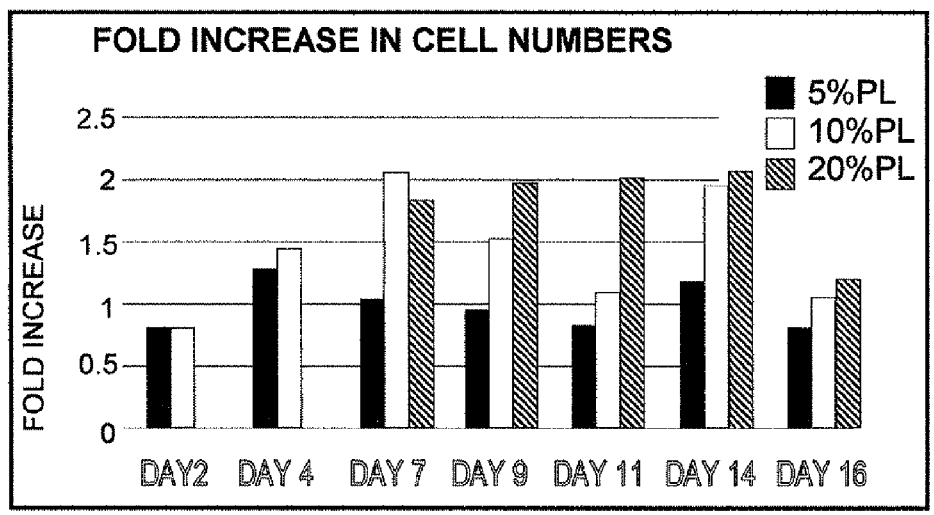
Figure 3E:
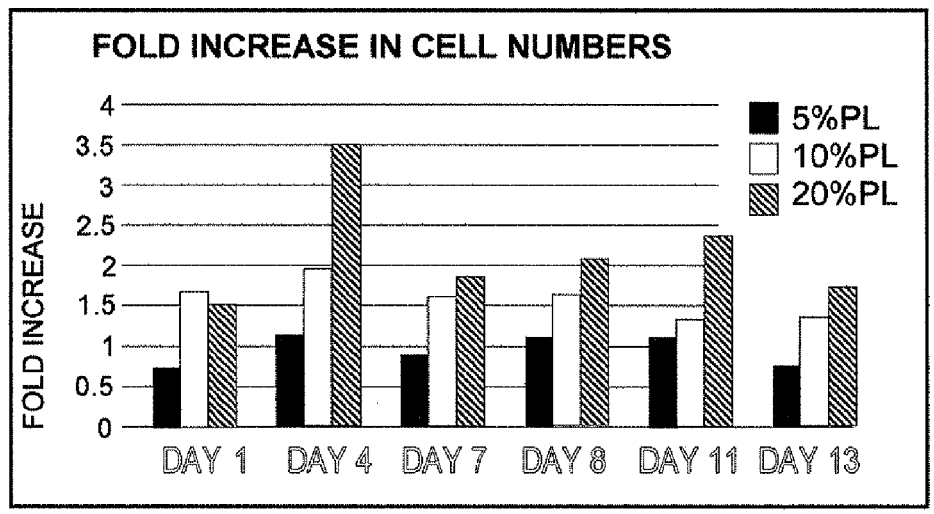

FIG. 2 is a cell expansion plot illustrating differences in yield and rate of growth between eight osteoarthritic patient's cells when those cells were grown in vitro in 5-10% platelet lysate.

FIGS. 3A-E illustrate bar graphs for 5 patient isolated MSC populations over a course of 1 to 6-16 days using from 5-20% platelet lysate.

Figure 4:
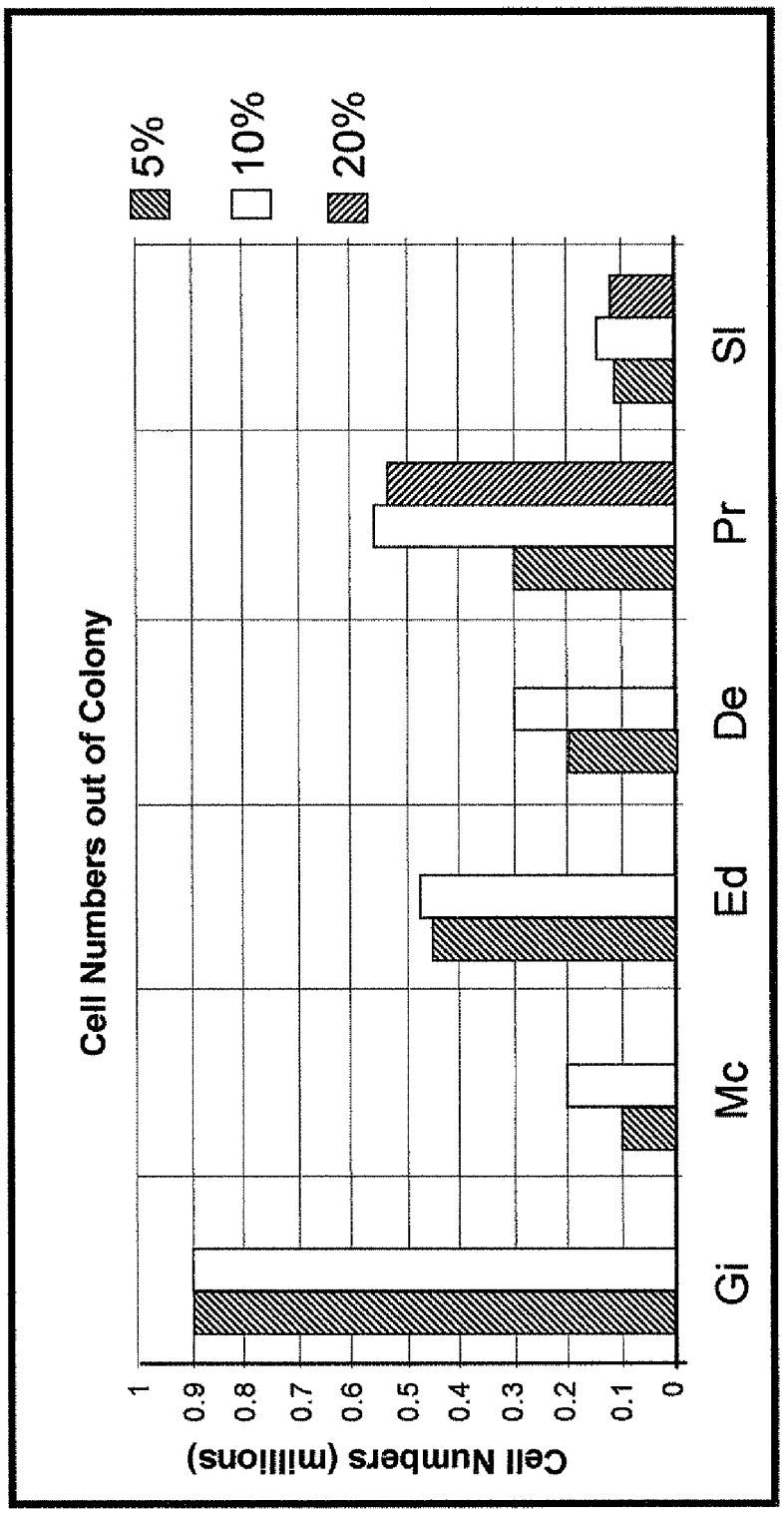

FIG. 4 illustrates a bar graph for 6 different patient MSC expansions using from 5-20% platelet lysate where patients cells showed either slow growth or fast growth.

Figure 5:
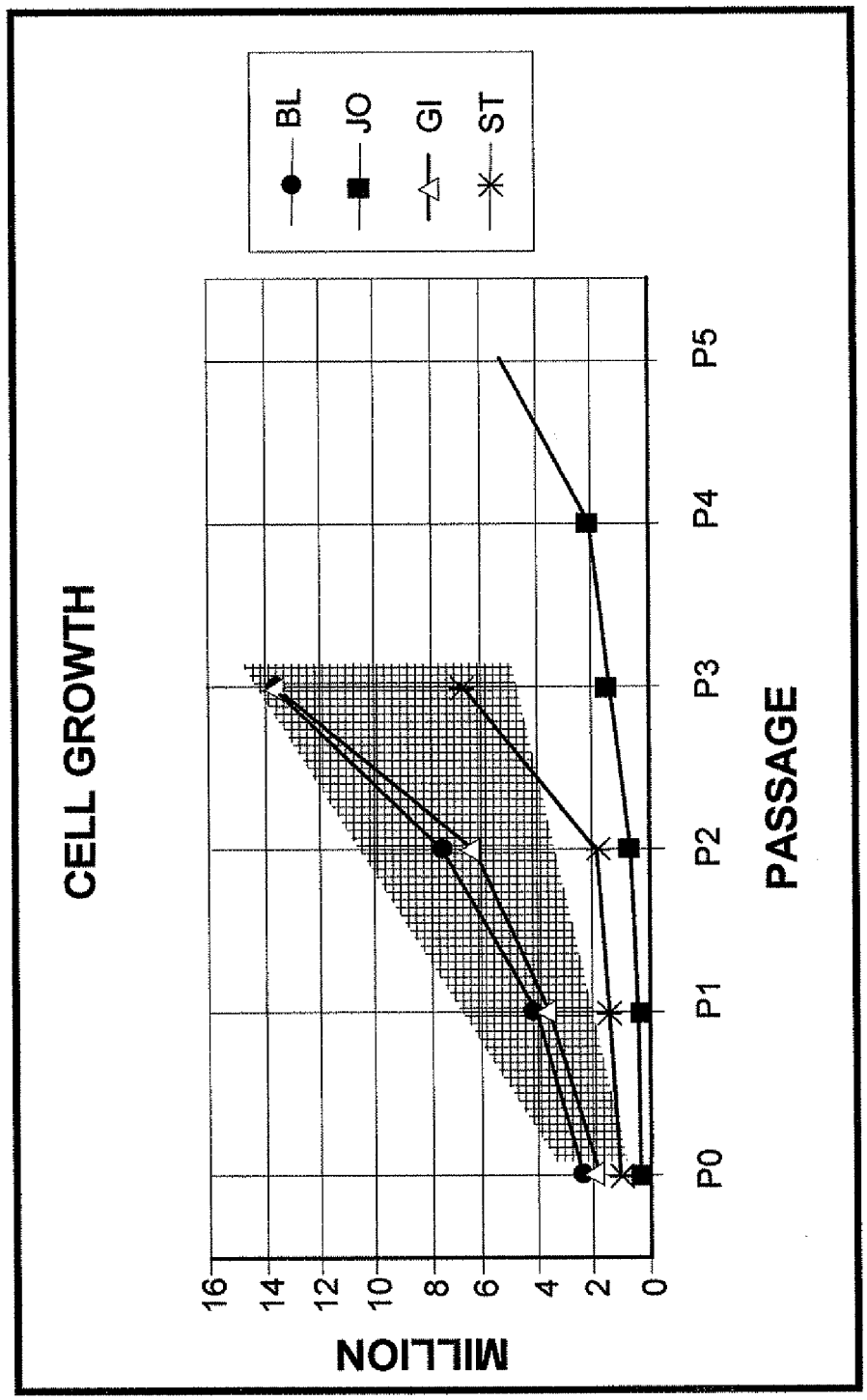

FIG. 5 is a stem cell growth channel overlay for 5 different patients.

Figure 6A:
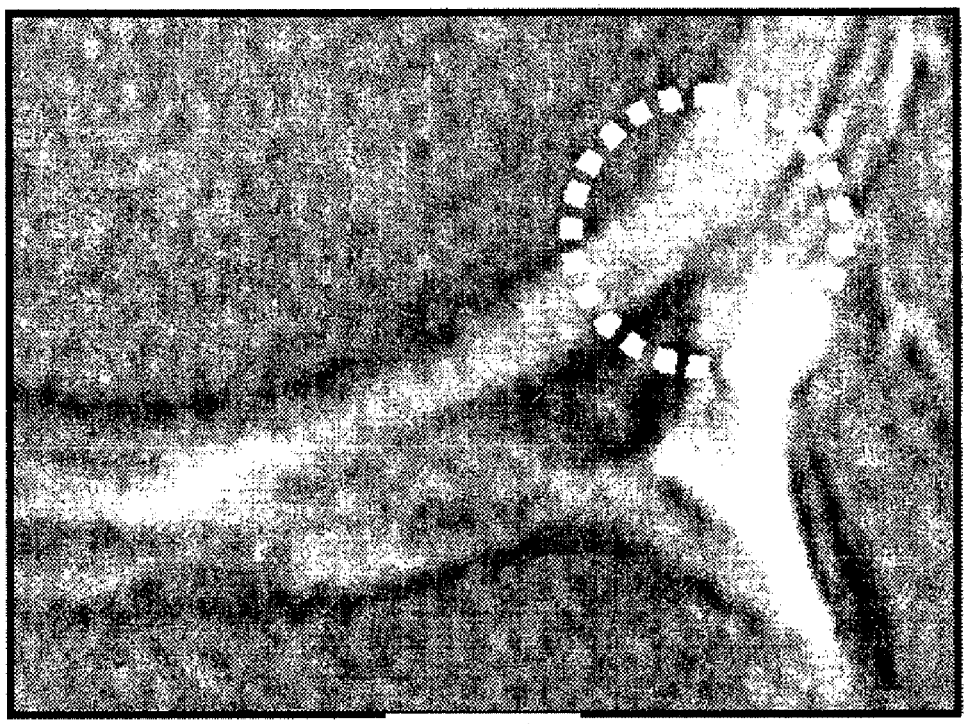

FIGS. 6A and B are before and after "fast spin proton density images" for a MSC implantation using cells optimized by embodiments of the present invention.

Figure 7:
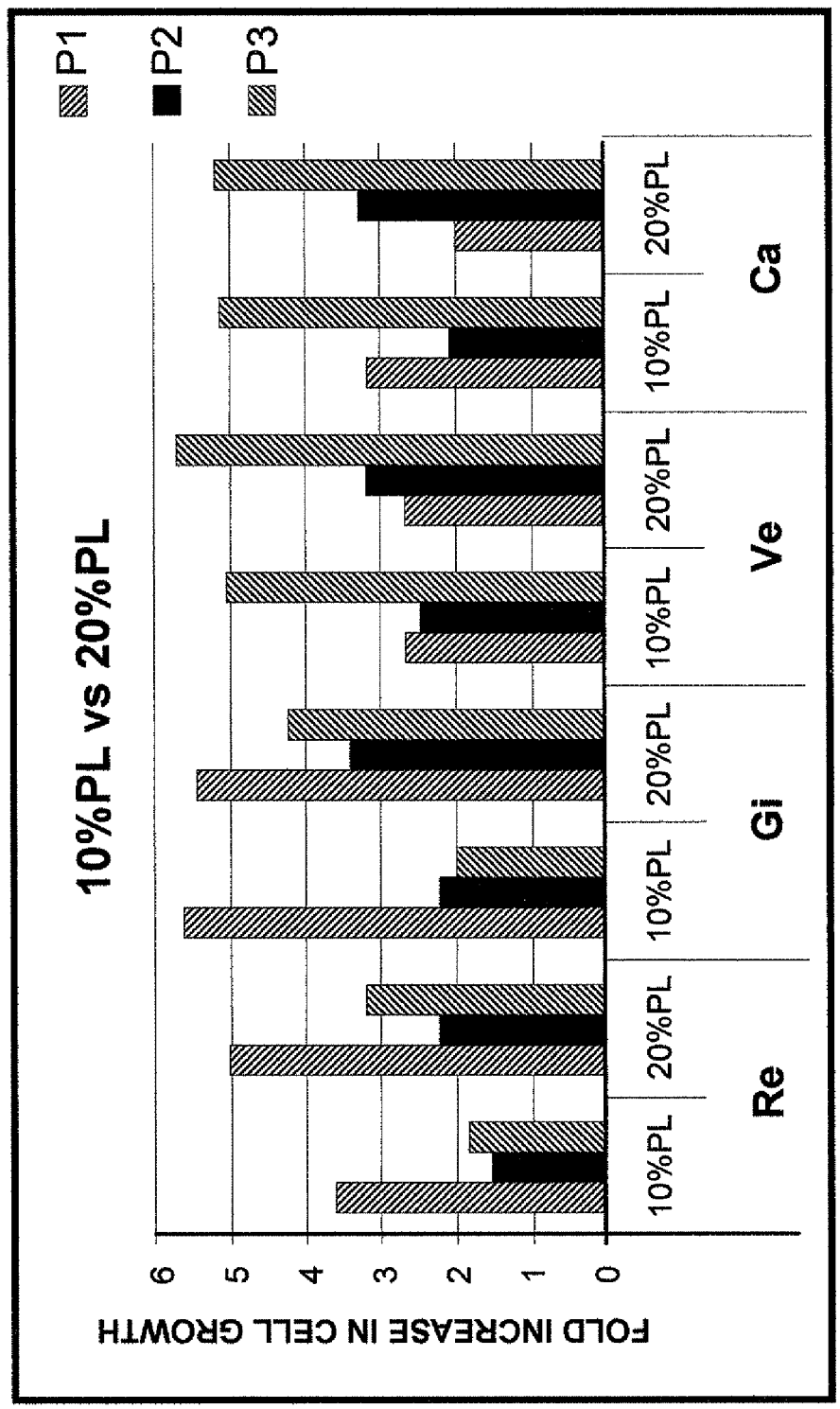

FIG. 7 is a bar plot illustrating 4 patients cell growth using 10 or 20% platelet lysate as introduced either at a first passage, second passage or third passage.

Figure 8:
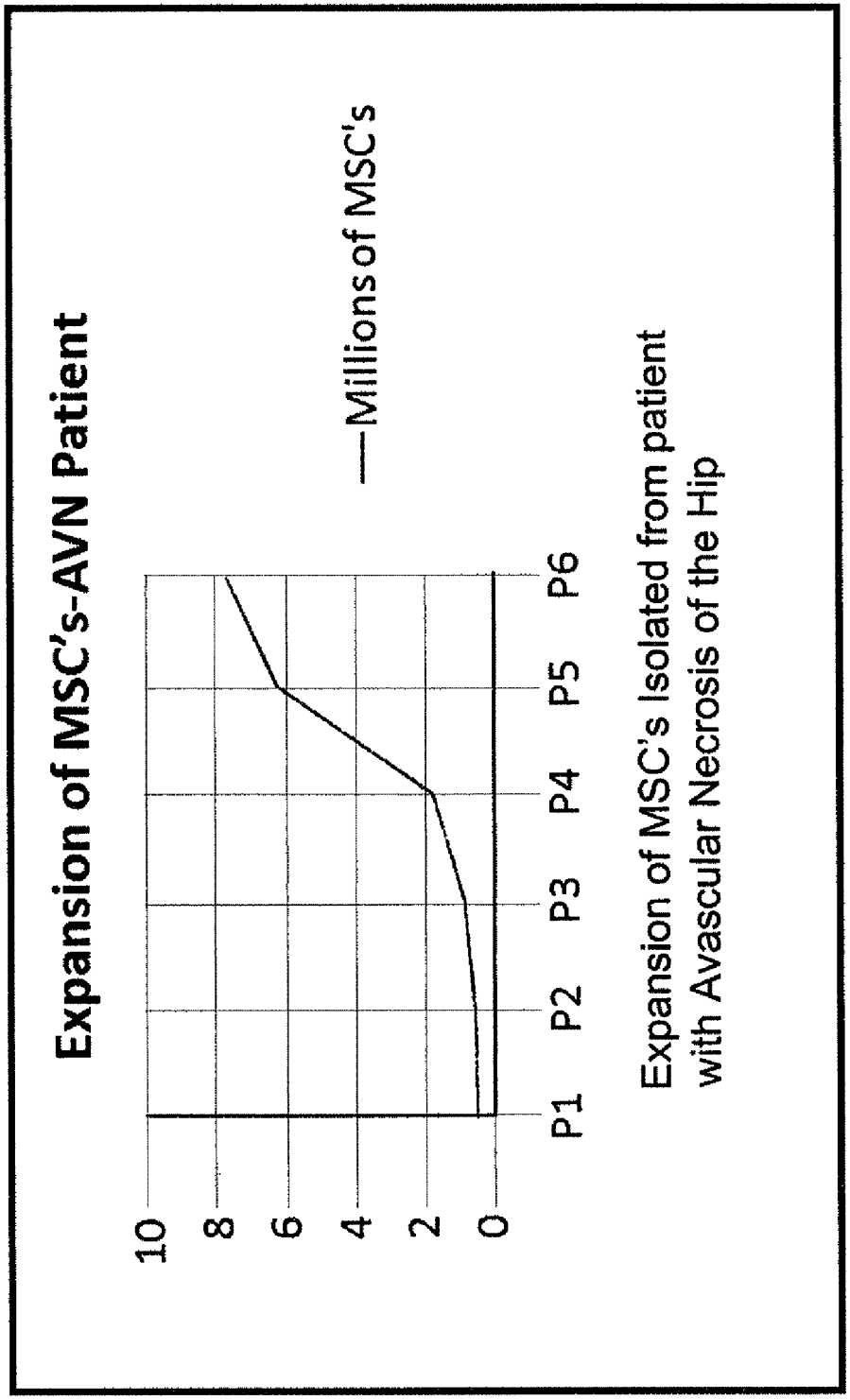

FIG. 8 shows cell expansion for a patient with stage 3-4 Avascular Necrosis under two different marrow draw conditions. Condition 1: Two 10 cc marrow draws yielded 48 million nucleated cells which failed to expand in 10% platelet lysate. Culture was aborted after 2 weeks. Condition 2: six small aliquots of 1-2 cc of marrow taken from the bilateral PSIS area yielded 164 million nucleated cells. The expansion plot for MSC's grown in 20% platelet lysate is shown.

Figure 9A:
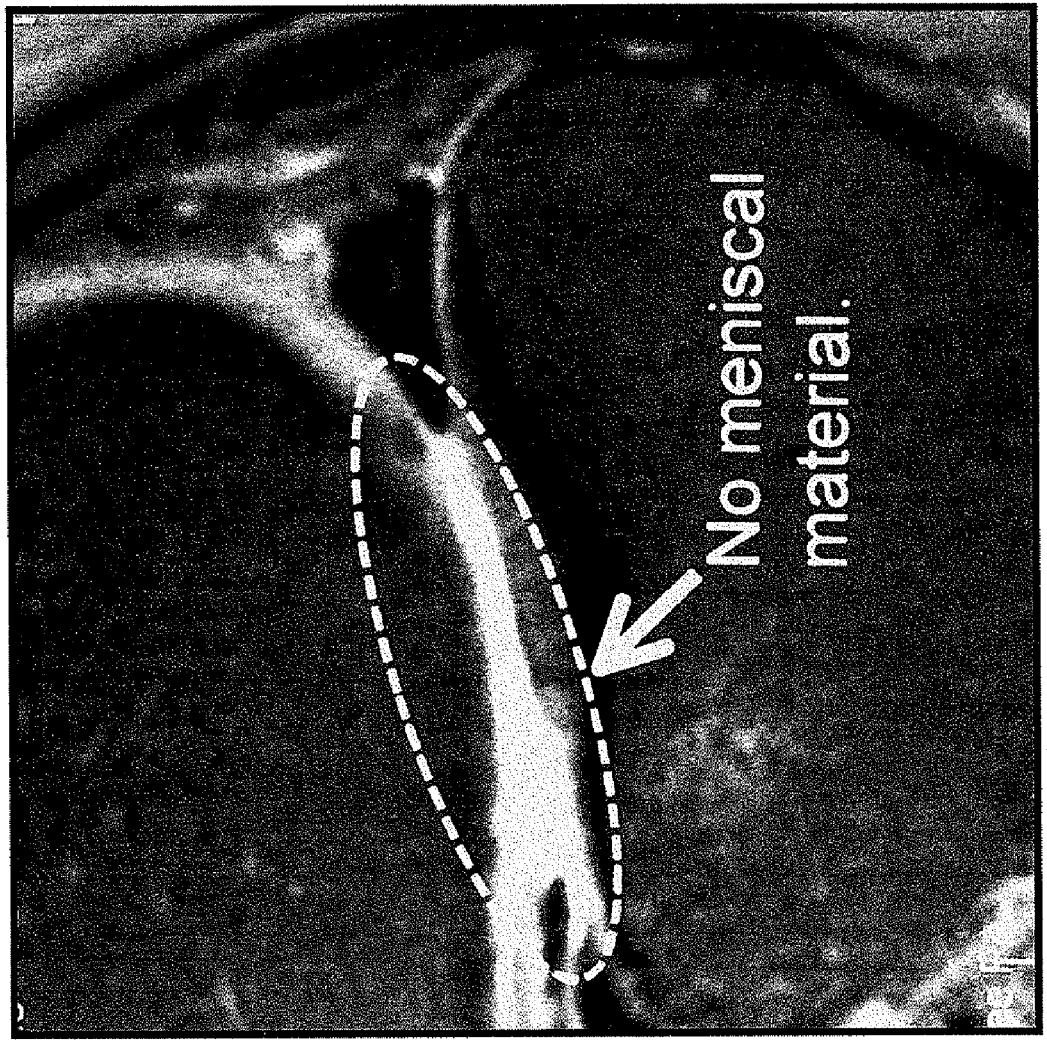
Figure 9B:
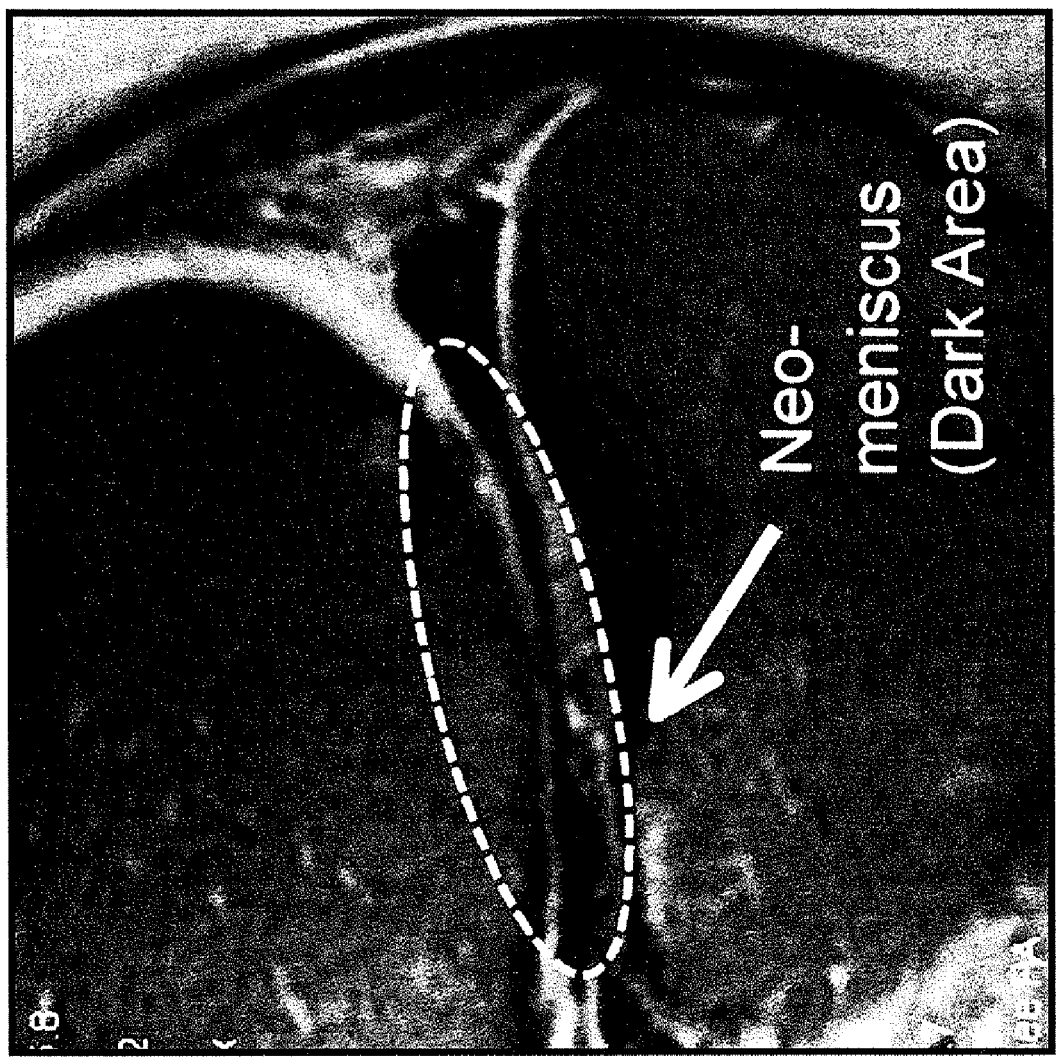

FIGS. 9A and 9B are before and after "fast spin proton density MRI images" for a MSC implantation using cells optimized by embodiments of the present invention. Partial regeneration of the anterior-medial knee meniscus is shown. Expansion of MSC's isolated from patient with Avascular Necrosis of the hip. Continuing matching image sequence of the right knee before cells (left image in January 2007), then 3 months after cells (right image in June 2007).

Figure 10A:
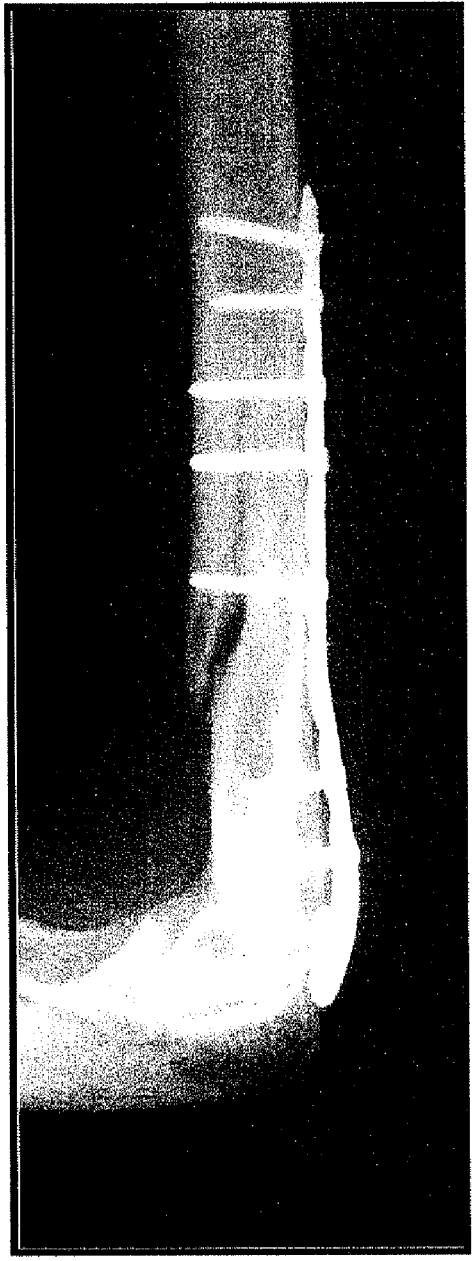
Figure 10B:
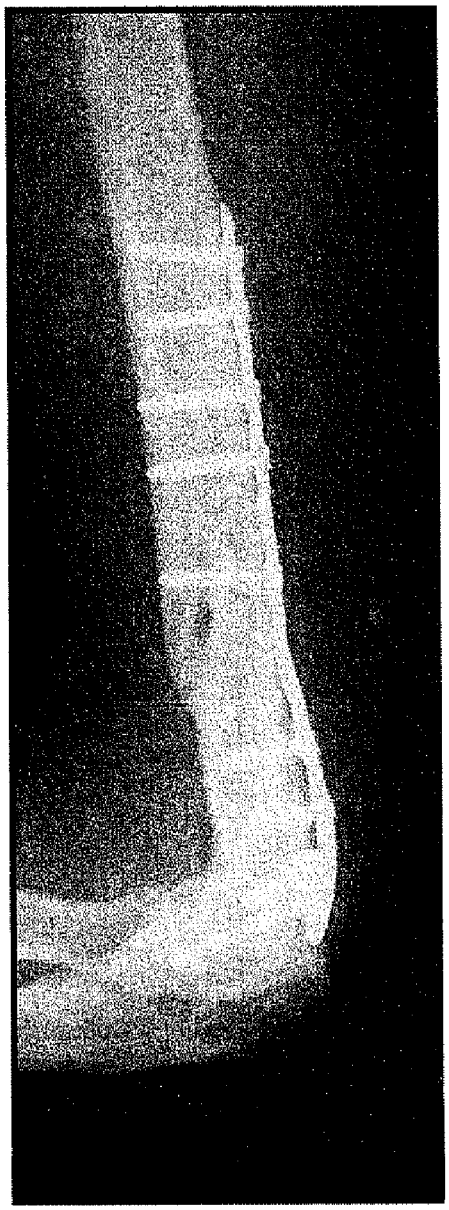

FIGS. 10A and 10B are before and after radiographs for a MSC implantation using cells optimized by embodiments of the present invention. Partial healing of humerus nonunion fracture is shown. FIG. 10A is a nine month old fracture non-union of the humerus that had failed a trial of a bone stimulator. FIG. 10B is five weeks after percutaneous introduction of MSC's expanded through the invention described herein. The fracture site has healed and approximated with only one small area of lucency.

Figure 11A:
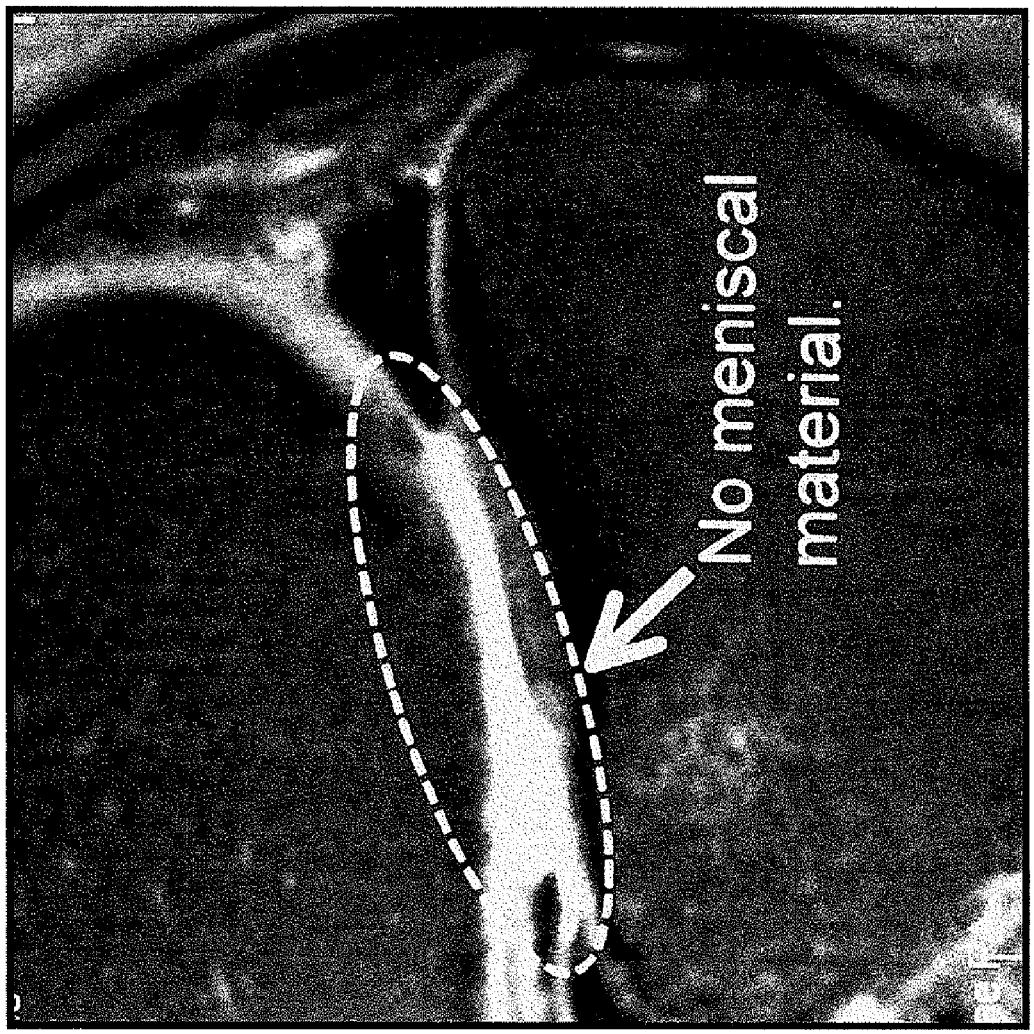
Figure 11B:
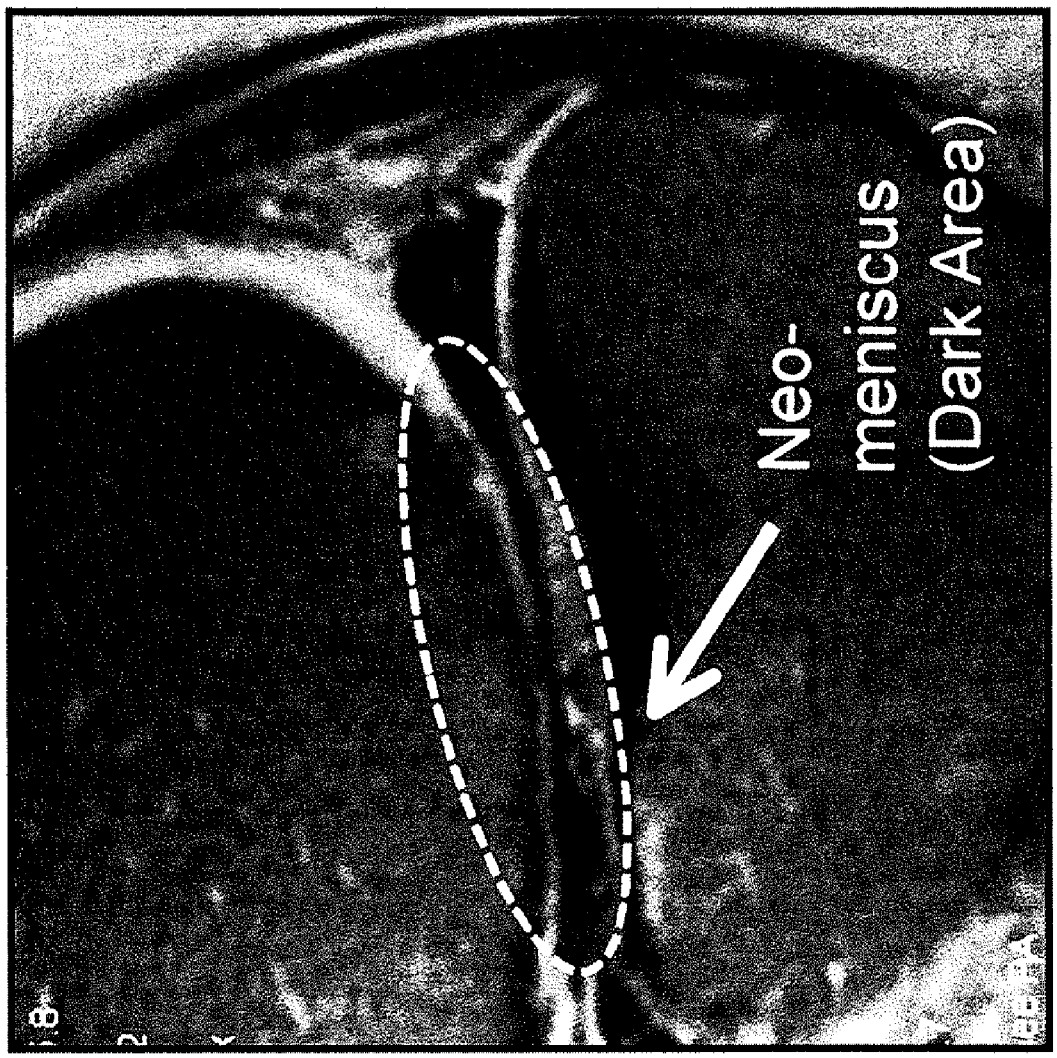

FIGS. 11A and 11B are before and after sagittal proton density images of an osteoarthritis patient with a severely degenerated medial meniscus and subsequent regeneration of parts of that meniscus using MSC's expanded using the embodiments of this invention. (A) is a 3.0T MRI sagittal proton density image of the knee joint demonstrating severe medial meniscus degeneration in an osteoarthritis patient. (B) is the same image parameters showing re-growth of meniscus, three months after percutaneous implantation of MSC's expanded using the embodiments of this invention.

DETAILED DESCRIPTION OF THE INVENTION

Embodiments of the invention provide compositions and methods for the harvest, expansion and implantation of autologous mesenchymal stem cells under optimal growth conditions. Expansion conditions are based on individualized growth characteristics for the patient's particular MSC population, not requiring synthetic or recombinant growth factors. In typical embodiments the optimal growth conditions are at least partially provided by platelet lysate from the same patient. These platelet lysate compositions provide a consistent and effective release of the patient's own combination of growth factors. Note that aspects of the invention equally apply to other cell types besides MSCs, e.g., stem cells, chondrocytes, etc., but for convenience embodiments described herein will be directed toward MSCs. Further, optimally grown cells can be implanted in combination with autologous factors to enhance the cells capacity for enhanced therapeutic results, for example in combination with platelets or platelet lysate, i.e., platelets harvested from the same patient that will receive the MSCs. Finally, embodiments of the invention described herein include MSCs enriched for a homogeneous phenotype that results from the optimized growth conditions described herein, such cells are identified as cells optimized for use in regenerative MSC-based therapy.

DEFINITIONS

The following definitions are provided to facilitate understanding of certain terms used frequently herein and are not meant to limit the scope of the present disclosure.

"Individualized growth characteristic" refers to individual specific ex vivo growth characteristics of harvested cells. For example, cells typically harvested from many individuals having osteoarthritis show slow growth, requiring modified growth characteristics to ensure that the cells have optimal growth and therefore are prepared for implantation back into a patient.

"Mesenchymal stem cell" or "MSCs" refers to multipotent stem cells capable of differentiating into osteoblasts, chondrocytes, myocytes, adipocytes, neuronal cells, pancreatic islet cells, and the like (see below).

"Natural expansion factor" refers to factors that are native to a patient in need thereof as opposed to synthetic or recombinant expansion factors that are prepared from in vitro sources. Natural expansion factors are typically associated with and released from a platelet lysate.

"Platelet lysate" refers to the combination of natural growth factors contained in platelets that has been released through lysing those platelets. This can be accomplished through chemical means (i.e. $CaCl_2$), osmotic means (use of distilled $H_2O$), or through freezing/thawing procedures. Platelet lysates of the invention can also be derived from whole blood and can be prepared as described in U.S. Pat. No. 5,198,357, which is incorporated by reference herein.

"Protein," "peptide," and "polypeptide" are used interchangeably to denote an amino acid polymer or a set of two or more interacting or bound amino acid polymers.

"Stem cells" refers to any cell having the characteristic of being unspecialized and able to renew for extended periods of time through cell division and being inducible to become cells with specialized function.

"Cell Culture Action" refers to a change in platelet lysate concentration, reseeding of cells in culture at a different density, or a change in planned passaging time (i.e. leave in culture a longer or shorter time before medium change).

"Passage" refers to changing spent medium in a monolayer culture or otherwise changing medium to improve the cell culture microenvironment.

Source of MSCs and Platelet Lysates

Mesenchymal stem cells are multipotent stem cells located in the bone marrow, peripheral blood, adipose tissue and other like sources. MSCs have the capacity to differentiate into a number of cell types, including osteoblasts, chondrocytes, myocytes, adipocytes, and beta-pancreatic islet cells.

Source MSCs of the invention are typically harvested from the iliac crest of the patient in need of the restorative/replacement therapy (or a suitable donor), such patient is referred to herein as a "patient in need thereof" (note that other sources, such as adipose tissue, synovial tissue, and connective tissue have recently been identified and are also considered as MSC sources within the scope of the present invention). In one embodiment, approximately 10-20 cc of bone marrow is harvested and "isolated" using methods described in U.S. Patent Application 60/761,441 to Centeno or through adherence to plastic, as described in U.S. Pat. No. 5,486,359 to Caplan et al. Each of these references is incorporated herein in their entirety for all purposes.

This invention also incorporates changes to standard marrow draw procedures to allow appropriate nucleated cell number yield to use the platelet lysate techniques described. Since the vast majority of the published research is again performed in healthy humans or animals, the application of this technique to humans with various disease states has never been tested. An example is shown is FIG. 8, where a marrow draw from a patient with AVN (in need of bony repair at an AVN site) and using the bilateral 10 cc draw technique described above produced a failed culture expansion in platelet lysate. However, the use of an altered technique drawing three small 2-3 cc marrow aliquots on each side (total of 6 aliquots), produced the required nucleated cell yield which was successfully expanded in 20% platelet lysate.

Platelet lysate for use herein is prepared from the bone marrow harvest using the method of Doucet, which is incorporated by reference herein in its entirety. Typical lysates include from about tens of millions to 100's of billions platelets. As shown by Martineau et al., Biomaterials, 2004 25(18) p 4489-503 (incorporated herein by reference in its entirety), platelet lysates inherently include the growth factors required to facilitate consistent MSC growth. In typical embodiments the platelet lysate and MSC are autologous and are in amounts useful for effective and consistent expansion of the MSCs (described more fully below). In particular, it should be noted that while the levels of growth factors such as TGF-beta are much lower in platelet lysate than those commonly used to expand MSC's, it is believed that there are significant synergistic effects when all of the low level growth factors contained in platelet lysate are used together.

Growth Channel Considerations

As discovered by the inventors herein, harvested MSCs of the invention provide optimal restorative/regenerative therapy when implanted back into a patient by no later than the $10^{th}$ ex-vivo passage, and preferably no later than the $5^{th}$ ex-vivo passage (one passage being equivalent to harvest and plating of cells to allow for enhanced cell numbers for medium and/or tissue culture housing/substrate). As such, each patient's MSCs must be expanded to the necessary numbers, for their therapeutic use, in a limited number of passages without drugs or growth factors that are not FDA approved. Embodiments of the invention provide growth channel conditions for ensuring that harvested MSCs are expanded to the required amount using platelet lysates and are therefore optimized for implantation and use in the target patient.

Various considerations exist for determining a patient's MSC growth potential (for ensuring the required number of cells), i.e., individualized growth characteristics (see definition above). These considerations include the source of the MSCs, i.e., age, gender, hereditary restrains and presence of degenerative disorders like osteoarthritis.

With regard to MSC's harvested from patients having osteoarthritis, the inventors have identified two different cell growth types: "slow growth" and "fast growth." The presence of slow growth cells in a patient presents a practical problem, the ability to expand cells quickly and keep maximum differentiation potential within this group of cells. Cells that are not in maximum differentiation potential are likely to fail during implantation. Crisostomo et al., Shock, 2006 26(6): p 575-80. Therefore, higher levels of the patient's platelet lysate are required to stimulate the required MSC growth. As a result, these cells must be treated quite differently from MSCs isolated from a young, healthy individual. Note that cells showing limited ex vivo expansion potential, i.e., cells increase in number by less than 100% over the course of a passage time (<3 days) are considered slow growth for purposes of this invention.

In one embodiment of the invention, the amount of platelet lysate required for optimum MSC ex-vivo culture expansion is determined from monitoring harvested cells for growth under various growth conditions. This is particularly important where the cells are associated with a patient having osteoarthritis, osteoporosis, AVN, or other diseases of bone, cartilage, or connective tissue. MSC expansion is dependent on a number of variables: amount of growth factors in patients' platelet lysate (therefore modifying the % lysate required to maximize cell growth), the bioavailability of those growth factors (i.e., effect of these factors on the patient's cells), the relative concentration of those growth factors, and quality/quantity of patients' starting source cells. In one embodiment of this invention, to optimize the MSC growth under these variables a "growth channel" has been developed herein, i.e., the targeted expansion rate of a patients' cells in relation to a predetermined amount of time and/or cell passages (not more than 10 passages for optimal growth conditions). This growth channel takes into account all of the necessary cell culture decisions needed to produce a specific homogeneous cell population.

In one embodiment of the invention, the amount of platelet lysate required for targeted MSC ex-vivo culture expansion is combined with visual parameters to determine the optimum growth conditions. In particular, this embodiment requires that platelet lysate considerations discussed above be combined with consideration of colony formation of the harvested MSC and monolayer expansion of the MSCs. In one aspect, during colony formation the MSCs must be prevented from overgrowth, i.e., cells on the edge of the colony enclosing the colony must be prevented. In another aspect, during colony formation the MSCs must be prevented from undergrowth, i.e., cells not expanding. If MSCs during colony formation overgrow, they must be removed from the colony formation culture and placed into monolayer culture and if MSCs during colony formation undergrow, the medium should be partially removed (approximately half) and replaced with fresh medium (plus at least the previously used platelet lysate concentration). In another aspect, cells in monolayer expansion must be viewed for overgrowth, i.e., high density, and reseeded at, for example, 10,000-12,000 cells/cm$^2$ or undergrowth where cell morphology shows rounded, flag, or bloated cell shape. When cells show this morphology the platelet lysate concentration should be increased to at least 10-15% platelet lysate.

More specifically, the "Growth Channel" herein described for maximum expansion and repair capabilities for cells grown in platelet lysate encompasses four different aspects:

1. Cell Growth Rate in Monolayer Culture;
2. Cell Density in Monolayer Culture;
3. Cell Culture Pattern in Monolayer Culture; and
4. Cell Morphology in Monolayer Culture.

Figure 1B:
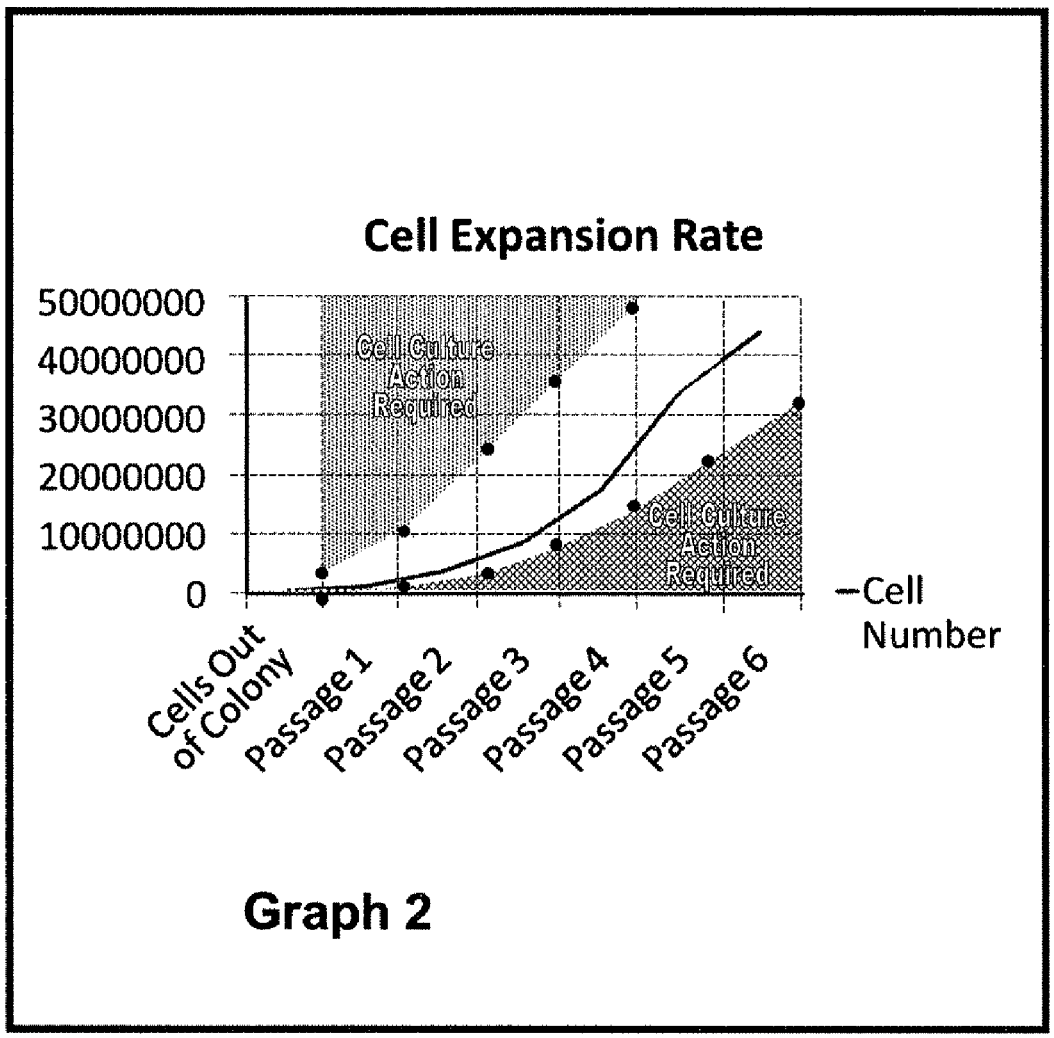
Figure 1C:
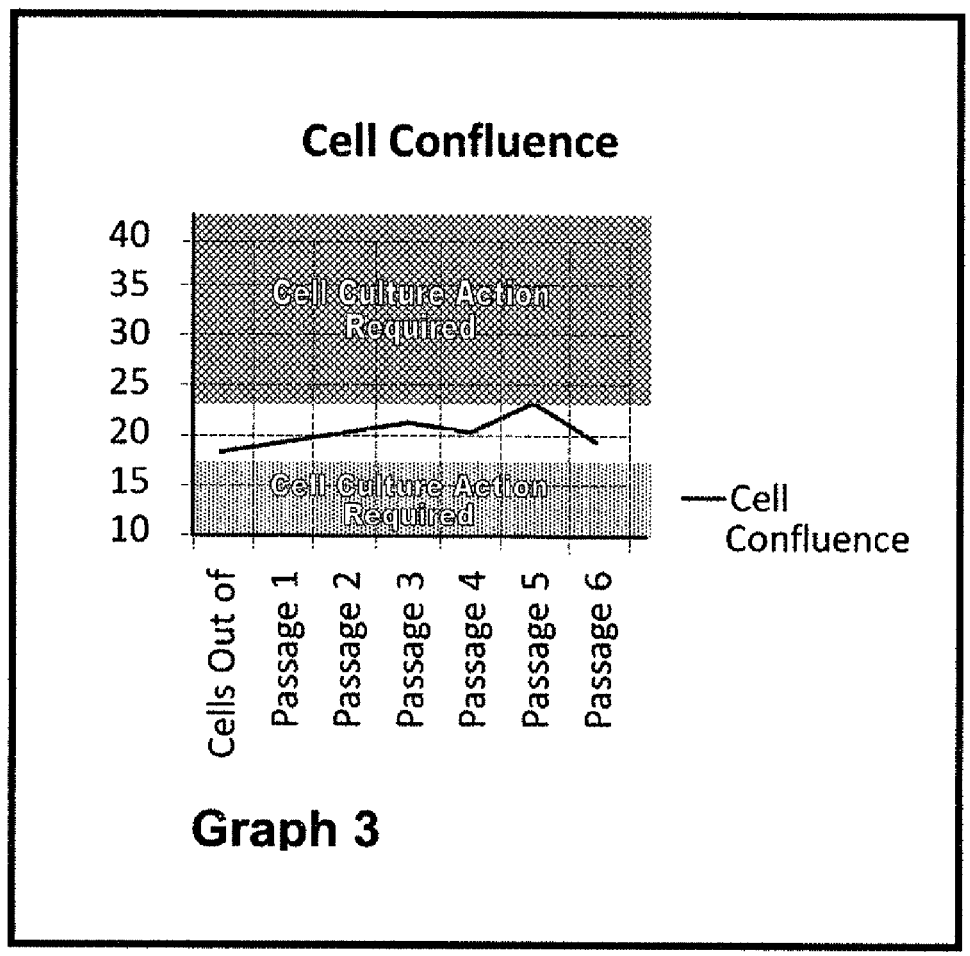

These concepts are also explained further in graphical format in FIG. 1.

"Cell Growth Rate in Monolayer Culture"-Since platelet lysate has variable levels of growth factor from patient to patient, there is no method to determine the biologic activity of those factors until their impact on culture expansion rates are accessed. As such, one key component of expansion within the "Growth Channel" is a minimum rate of growth. This is defined as adjusting the parameters of platelet lysate concentration and/or seeding density until doubling time is between 1 and 3 days. This will accomplish approximately a 50-100 fold increase in cells before the 5th-7th passage (FIG. 1, Graph 1). Also shown in FIG. 1 (graph 2) is an exemplar of a growth rate channel beginning with a bilateral 10 cc marrow draw (used for illustration purposes only). Deviation from the growth channel discussed above would require a cell culture action as described in FIG. 1, graph 1 and associated descriptions. "Cell Density in Monolayer Culture:"—Cell density can impact cell growth and differentiation capacity. Doucet (referenced above) described a very low seeding density of approximately several thousand cells per milliliter (in otherwise healthy controls). However, we have found that patients with diseases such as osteoarthritis, AVN, and fracture nonunion require a much higher seeding density and that maintaining that density during passage is critical to producing expanded cells capable of repair. As such, FIG. 1, graph 3 shows the acceptable cell confluence channel for an embodiment of this invention (to optimize the in-vivo repair capabilities of the cells). Spatial distribution of MSC's described by this invention can be quantified by the following equation: Surface area*(% Confluence)/Cell number. This Figure should be in the range of 18-23. If the value <18, then the cells can be seeded at a lower seeding density as they are growing exceptionally well. If this value falls between 23-27, then the cells should be seeded at a higher seeding density (from $12 \times 10^3$ cells/cm$^2$ to $15 \times 10^3$ cells/cm$^2$). And if this value is >27 then the platelet lysate concentration also should be increased.

Cell Culture Pattern in Monolayer Culture—The pattern of cell growth is important in this invention as evenly distributed distance between cells is required to promote continued expansion and maintain cells in an undifferentiated state. To ensure this, evenly distributed MSC's are the part of the growth channel described herein. This is further illustrated in FIG. 1, graph 4. Any deviation from the cell culture pattern discussed above would require a cell culture action as described in FIG. 1, graph 4 and associated descriptions.

Cell Morphology in Monolayer Culture: The cell morphology in monolayer culture is important to insure a specific MSC phenotype associated with this invention. Only as it applies to mesenchymal stem cells, the preferred morphology is spindle shaped (fibroblastic) in monolayer culture. It should be noted that other mesenchymal stem cells lines often appear to have a polygonal or flag shaped morphology, which is not the phenotype in the growth channel as described. Note that a classification system has been established for the purposes of this invention which encompasses types 1-4, with the preferred cell type associated with this invention as type 1. This is further illustrated in FIG. 1, graph 5. One should note that grades 2-4 displayed as part of FIG. 1, graph 5 are from the prior art and each of the cited authors considered these to be acceptable morphology for their MSC lines. Again, the preferred morphology to stay within the described growth channel is spindle shaped with the cell occupying little surface area, unlike the MSC's in types 2-4 which occupy approximately 50% more surface area than the optimal type 1 cells. Once the culture has >30% of grade 2-4 MSC's, the concentration of platelet lysate should be increased from 10% to 15-20%. The cell population should be transplanted at this point to avoid the potential deviation from the ideal morphology.

Any deviation from the cell morphology channel discussed above would require a cell culture action as described in FIG. 1, graph 5 and associated descriptions.

In one embodiment, a growth channel represents the growth characteristics of autologous MSCs in ex vivo culture required to obtain 10 million to 100 million cells for implantation into a target site, a knee joint for example. The number of expanded cells is somewhat dependent on the target site in need of regeneration, for example regeneration of a vertebral disc requires approximately 1-10 million cells per ml whereas the number for a knee surface requires approximately tens to hundreds of millions of cells per ml. Harvested cells are monitored and growth modified through the use of varying amounts of autologous platelet lysate.

Ex vivo expanded MSCs of the invention can be monitored for growth via cell counting techniques and/or through visual cell culture parameters. Cell counting techniques are based on harvesting and passing cells from a tissue culture housing or substrate when the number of cells has exceeding the available space/density for those cells. Cell counting techniques must be performed on site by a qualified technician who can harvest and count the cells in a counting chamber device, such as a hemocytometer, or spectrophotometically. As described elsewhere as part of this invention, cell counting can also be performed remotely through transmission of digital images via the internet to an experienced technician.

As discussed above, visual cell culture parameters disclosed herein include the capacity to visually inspect the cells of the invention to determine the readiness of cells to be harvested and re-plated. Visual parameters include cell culture morphology, cell culture pattern and cell culture density. In particular, the following specific qualitative parameters can be viewed: colony formation overgrowth, colony formation undergrowth, monolayer expansion culture overgrowth, monolayer expansion culture undergrowth, images of the hemacytometer for platelet and stem cell count; number of cells sticking when first seeded into a flask after the marrow draw; colony formation and later developed colonies to determine when the cells should be picked (including overgrowth and undergrowth); how evenly the cells are seeded into flasks, i.e., cells should be uniform within flask during monolayer expansion; how densely cells are seeded; stages of confluence as well as visualizing cell division to determine when the cells are ready for passage; how bloody the flask looks when the cells are in a colony; separation of blood after it is spun down to obtain platelets; what the separation in the marrow should look like after spinning it down to separate the nucleated cells from the red blood cells; and cell morphology, i.e., bloated, bright balls, spread out.

Visual inspection of target cultures can be performed either on-site via trained tissue culture personnel, remotely via a digital microscopy video technology (live feed) or via updated pictures taken by a digital microscope camera over the course of the growth channel procedures discussed herein. Remote monitoring of cell cultures can be performed where more limited control over multiple cell culture sites are required. For example, where a highly trained specialist of specialists are provided visual data from a number of off-site cultures. The highly trained specialist would have access to information that would validate the use of certain visual parameters, e.g., a particular cell density, culture pattern, or morphology that has provided good clinical results for knee joint regeneration, avascular necrosis stabilization, healing of bony non-union fractures, etc. The specialist would then know to associate that culture morphology with all such cultures (whereas a high number of on-site personnel may not make this correlation for many months or years, if ever). In one embodiment, cells having consistent, non-overgrown, cell culture morphology would be considered optimal and within the growth channel and therefore ready for harvest and re-plating.

Platelet lysate compositions of the invention include a number of growth factors known to be necessary for cell mitosis, including: hFGF, PDGF-BB, TGF-$\beta$, and VEGF. Platelet lysate compositions are added to serum free growth medium to obtain the targeted amount of lysate in the medium, for example, a 10% platelet lysate includes by volume 10% platelet lysate composition. In preferred embodiments the serum free basal medium is DMEM, Hams F12, MEM, or other like medium. Amounts of useful growth factors are inherent to a patient's platelet lysate and will typically vary from patient to patient.

In typical embodiments, cells from a patient are initially cultured in a medium having 10% platelet lysate for 7-10 days in colony formation and then recounted (colony formation). If the patient has osteoarthritis, the cells are transferred to monolayer culture using a starting 10% platelet lysate. Cells are grown for 2-4 days and compared to the total number of cells required for the particular patient's therapeutic procedure. In some embodiments the cells are visually inspected. Cells that are not within the growth channels described above will have their culture medium modified to an enhanced amount of platelet lysate (for example 15-20%), whereas cells that are within the channel will be allowed to proceed for at least 2-4 days before the procedure is repeated. Other cell culture actions that depend on channel conditions include reseeding cells at a lower or higher density, changing medium more or less frequently, or transplanting cells sooner or later. Note that visual parameters can also be utilized to determine whether the cells are within the growth channels described (see above).

Note that variability of MSC expansion rates are dependent both on the patient's harvested MSCs as well as based on the levels of growth factors within the patient's platelets. As such, in certain instances, higher levels of required platelet lysate to keep a patient's MSC within the growth channel are due to, not only the cells growth characteristics, but also on needing more platelets to provide the required levels of growth factors, i.e., where the patient's platelet lysate may have a lower concentration of growth factors as compared to other platelet lysates. Surprisingly, the inventors herein have determined that cells grown under optimal conditions are much more capable of achieving a therapeutic result as compared to a same number of cells grown under non-optimal (non-growth channel) conditions (for example a culture of cells that require 15 passages to have a sufficient number to perform the required therapeutic result). For example, the inventors have discovered that cells grown for less optimal expansion using a 10 cc bilateral PSIS marrow draw (total 20 cc marrow) have produced poorer clinical results (no or less cartilage regeneration noted on follow-up MRI, no or less meniscus regeneration) as compared to cells optimally expanded using the growth channels methodology described herein.

Method for Autologous MSC Replacement

Embodiments described herein include methods for the therapeutic restoration of a site in a patient in need thereof.

For example, therapeutic restoration of a degenerative disc or cartilage of a joint in need thereof. Other examples include the expansion of MSC's for cardiac muscle regeneration, cutaneous wound healing, healing of fracture or bony non-unions, neural repair, treatment of graft vs. host and other immune applications, and other uses, replacement of pancreatic islet cells, treatment of osteoporosis, treatment of hearing loss, and other uses. Methods described herein utilize autologous MSC restorative therapy where the MSCs are treated with natural (non-synthetic/non-recombinant) growth factors (typically obtained by culture with varying percent platelet lysate).

Initially, a MSC source is harvested from a patient in need of stem cell therapeutic restoration. The harvested source is maintained in a sterile environment and under sterile conditions throughout the procedure. As discussed previously herein, the harvested cells are seeded and ex vivo cultured under conditions to maintain the cells within the growth channel embodiments of the invention (MSC isolation from a source is described above). This requires that platelet lysate from the patient be obtained and prepared, for example as described in Example 1. Autologous MSCs grown under optimal expansion conditions are monitored and prepared for implantation prior to the cells being passaged 10 times with a target yield of 10-100 million cells (a total number of cells for the target site are identified, see above). In some embodiments the autologous MSCs are grown and monitored for implantation prior to the cells being passaged 5 times with a target yield of 10-40 million cells. In other embodiments the autologous MSCs are grown and monitored for implantation prior to the cells being passaged 6, 7, 8 or 9 times with a target yield of 10-40 million cells. The prepared MSC composition is then implanted into the target site and monitored for effectiveness over the next several months. The procedure can be repeated dependent upon desired result. Cells that have been treated under conditions that result in 10 to 40 million cells within 4-7 passages, are optimal cells for implantation into a target site in a patient in need thereof.

In particular, in some embodiments, this invention also encompasses a novel method of seeding red blood cells with isolated marrow nucleated cells in initial colony formation and attachment culture. Since red blood cells also contain growth factors, this further supplements the cell growth environment and has other differentiating effects on the isolated MSC's.

Note that embodiments of this method are performed with autologous cells and growth factors thereby avoiding a number of immunologic and infectious issues inherent in other non-autologous MSC replacement therapies. This is of significant importance at this juncture, due to recent research demonstrating that non-autologous MSC's activate the natural killer cell system in the host. Spaggiari et al., Blood, 2006 107(4):1484-90; Rasmusson et al., Transplantation, 2003 76(8):1208-13. These embodiments also optimize the potential for the implanted cells to expand at the site and differentiate into the required cells (chondrocytes at a joint surface, osteoblast in a bone defect, etc). As described in the next embodiment, platelet lysate compositions (or platelets themselves) can also be injected into the site concurrently or subsequently to the MSC implantation.

Using the cell growth embodiments described herein, optimally grown cells are prepared for use in a target patient. Cells grown in accordance to embodiments described herein were tested using FACS to determine cell phenotype, i.e., determine the cells surface antigen profile. In one aspect of the invention, a cell population is selected and expanded to be positive for at least one of the following cell surface antigens: CD29, CD44, CD59, CD73, CD90, CD105 and CD166. Note that a positive result is one where at least 90% of the tested cells are positive by FACS analysis for the particular cell surface antigen.

In typical embodiments, identified cell populations are positive for at least two of the following cell surface antigens: CD29, CD44, CD59, CD73, CD90, CD105 and CD166. In more typical embodiments, cell populations are positive for at least three of the following cell surface antigens: CD29, CD44, CD59, CD73, CD90, CD105 and CD166. In even more typical embodiments, cell populations are positive for at least four of the following cell surface antigens: CD29, CD44, CD59, CD73, CD90, CD105 and CD166. In still more typical embodiments, cell populations are positive for at least five of the following cell surface antigens: CD29, CD44, CD59, CD73, CD90, CD105 and CD166. Finally, in some embodiment's cell populations described herein are positive for six or all seven of the CD29, CD44, CD59, CD73, CD90 and CD105 cell surface antigens. Cell embodiments having these potential cell surface antigens are shown herein to be optimal for purposes of therapeutic use. In addition, cell population embodiments herein have the above cell surface antigens but lack at least one of the following antigens: CD14, CD31, CD45 and CD106. In other embodiments the cell population embodiments herein have the above cell surface antigens but lack two or more of the following antigens: CD14, CD31, CD45 and CD106. In still other embodiments the cell population embodiments herein are positive for CD29, CD44, CD59, CD73, CD90, CD105 and CD166 cell surface antigens but negative for CD14, CD31, CD45 and CD106 cell surface antigens.

Direct Platelet Injection Into Target Site

In some embodiments of the invention a platelet composition is directly injected into a patient's target site. Platelet injections can be performed prior to MSC replacement, combined with MSC replacement (contemporaneous), or after MSC replacement to help optimize the MSC growth environment. In typical embodiments, MSCs expanded using the platelet lysate based medium and growth channel considerations of the invention are harvested (while they are in the growth channel) and injected into a target site with either autologous platelets or platelet lysate.

In order to determine the number of platelets required to inject directly into a site the following calculation can be performed. The first issue is to determine the average platelet number/cc required to sustain maximum ex vivo MSC growth. For example, if a patient's cells were shown to require a 10% platelet lysate for 3 days, a 20% platelet lysate for 3 days and a 30% platelet lysate for 3 days, the highest platelet lysate concentration is utilized in determining how much platelet supplementation is required at the site. The maximum usage of platelets per cc per day was 30% (for three days) in this example. If the starting volume of platelets per cc of volume for the patient was $1.0 \times 10^9$, during this time period $3 \times 10^8$ platelets used per cc of volume over three days or $1 \times 10^8$ platelets per cc per day is necessitated.

Marineau et al., Biomaterials, 2004 25(18): p 4489-502 (incorporated by reference herein for all purposes) provides insight into the levels of thrombin and calcium necessary to promote in vivo MSC growth via release of growth factors from platelets. This is a natural occurrence during the first weeks of development to promote tissue growth and angiogenesis. From these studies it can be deduced that activated platelets will release most of their cargo of growth factors upon activation with thrombin and calcium over a 7 day period. As such, the $1 \times 10^8$ platelets per cc per day is multiplied by 7 to provide the final amount of platelets required per cc—$7 \times 10^8$ platelets per cc. The final volume for injection into the patient is added to the initial fluid joint volume (IFJV), which represents the final fluid joint volume (FFJV). Therefore, using the above calculation, $7\times10^8$ platelets per cc is multiplied by 12.5 to yield $8.75\times10^9$ platelets. This number represents the final platelet dose (see formula 1):

(Average Platelet per cc to sustain MSC growth/Days at this level before medium change)×(Days at this level before medium change required((7) (Final fluid joint volume))=PHC Platelet Dose.   (Formula (I)).

Alternatively, the supplementation can be carried out using platelet lysate equivalent to the highest ex-vivo percentage required to promote expansion, adjusted for joint volume, and supplemented more frequently.

Site Monitoring of MSC Implantation

Implanted cells described herein can be monitored to ensure that these cells are surviving in-vivo and that the cells ultimately differentiate into the cell type required to obtain the needed repair. In one embodiment, MRI labeling is performed to allow for non-invasive monitoring of the patient's site (however, note that this procedure requires magnetic particles and only provides cell location, not cell expansion or differentiation state).

Real-time cell monitoring is therefore preferred. After transplantation of the optimally expanded cells, a percutaneous fluid wash is taken from the implantation site. Free floating cells and minimally adherent MSCs are obtained and examined for number of cells, type of cells, differentiation state of MSCs (if any), MSC appearance and for the MSCs state of proliferation. The joint wash can also be monitored or assayed for the expression of key substances such as glycoaminosglycans, key proteins, gene expression, or other important chemical or genetic indicators of improvement in the joint microevenvironment.

Two types of real-time monitoring can be performed: a random sampling of site fluid and/or a high pressure "knock-off" of site fluid. The high pressure "knock-off" is performed using a needle or catheter (typically equivalent to a 14-22 gauge) where high pressure fluid is pushed through to knock off minimally adherent MSCs.

Alternatively, needle arthroscopy or traditional arthroscopy to obtain tissue samples for analysis can also be used.

Percutaneous sampling is performed at baseline prior to the MSCs being transplanted (which form a sample which can be compared to all future samples). Sampling is also performed at 1 week, potentially at 2 weeks and potentially at 3 weeks post implantation of MSCs into the target site.

In particular, at one week post implant, a joint wash or tissue sample is taken and examined. While it is taken for granted that the cell population can be easily examined ex-vivo and adjustments to growth media made, without an in-vivo sampling method, the same needed adjustments can not be made to ensure in-vivo growth and engraftment. However, based on this real-time monitoring, changes in platelet and/or platelet lysate supplementation can be performed into the target site. This process can be repeated based on need. In addition, additional autologously cultured MSCs can be implanted into the site.

Finally, upon a determination that the implanted MSCs are alive and capable of proliferation and or that the joint microenvironment is appropriate for cell survival and engraftment, a differentiation agent can be contacted to the patient's site. In addition, cells obtained from the real-time monitoring analysis can be cultured in the presence of various differentiation agents to determine which agent is best suited for the required result. Illustrative agents include bone morphogenetic protein 2, dexamethasone, hyaluronic acid, and the like. In addition, where inflammatory cells are recovered in the real-time monitoring, an anti-inflammatory agent can be included in the treatment or where the site is dehydrated a hyaluronic acid can be added.

In addition, in-vivo post implantation of cells can be monitored using assay methods for other secondary effects of tissue regeneration such as production of glycoaminosglycans (GAG's), reduction in known degradative enzymes, and other factors. The important aspect of this portion of the invention is that direct or indirect monitoring of the cells continues after implantation. Again, this allows for real time changes in post-transplantation protocols to ensure cell survival and engraftment as well a function once differentiated. As an illustrative example, MSC's once differentiated into an early stage chondrocytes would be monitored for GAG production so that they would be considered fully functional and biologic equivalent of a mature and health chondrocyte. In addition, certain differentiating or supplemental substances may be introduced into the joint for the purposes of increasing the monitored GAG production. This same example could also be applied to other areas of tissue regeneration such as the replacement of pancreatic islet cells and the monitoring of insulin production from MSC's differentiating into islet cells in-vivo.

Therapeutic Applications

Methods and compositions of the present invention can be used to treat, i.e., repair or maintain a target site in a patient in need of a MSC application. Conditions that can be treated using the embodiments described herein include osteoarthritis, degenerative disc disease, cartilage replacement in joints, stabilization of a bony avascular necrosis site, healing of bony fracture or other bony non-unions, cardiac muscle regeneration, cortex repair, cutaneous wound healing, neural repair, cell therapy for immunosuppression or regulation, replacement of beta islet cells, replacement of cells and structures involved in hearing, treatment of osteoporosis, and other disorders where MSC's can differentiate into cells for repair and replacement of injured, missing, or degenerated cells.

EXAMPLES

The following examples are provided for illustrative purposes only and are not intended to limit the scope of the invention.

Example 1

Patients' MSC Growth in Relation to Growth Channel

Nucleated cells were harvested from a patient's posterior iliac crest and separated from the RBCs using centrifugation (serum is a gradient).

Approximately 10 ml of bone marrow was harvested from the target patient and transferred to a cell culture lab in a 15 ml centrifuge tube. The marrow sample was then spun down at 100 g for 2-3 minutes. The RBC pellet was checked to ensure that the bulk of the RBCs were in the lower half of the sample and that a clear zone exists between the RBC pellet and top fraction of material. Note that if the top fraction is not 40-50% of the total volume, the spin step will need to be repeated. The top fraction was then removed and placed in a 15 ml centrifuge tube and spun at 1000 g for 10 minutes. Note that the nucleated cell pellet may appear red and perhaps loosely packed, dependent on the number of RBCs present. The serum supernatant is removed and added back to the RBC pellet. The nucleated cell pellet is re-suspended in 1 ml of saline. The steps above were repeated to obtain additional nucleated cells.

The nucleated cells were then counted by diluting the suspension 1:20 in water (lysis RBCs) and counting nucleated cells. The RBCs were counted using a 1:2000 dilution.

Nucleated cells were then seeded for monolayer growth. For each $cm^2$ seed approximately $0.66$-$1.25 \times 10^6$ nucleated cells and $0.16 \times 10^9$ RBCs were combined (supplement RBCs in nucleated suspension with cells from RBC suspension). The combined cell mix was then spun at 1000 g for 10 minutes and re-suspended in DMEM+Cipro+heparin+10% platelet lysate (10% was chosen as a starting dose based on our data demonstrating a significant suboptimal expansion rate with 5% lysate as described by Doucet). The suspension was then warmed for 30 minutes at 37° C. The warmed suspension was plated into an appropriate sized tissue culture flask and fresh medium added. Cell culture was incubated for 7-12 days at 5% $CO^2$, 37° C.

As shown in FIG. 1, MSC growth from 8 patients were plated under the above conditions and plotted for growth as a function of cell number versus days. An acceptable growth channel has been overlaid onto the cell number expansion. As of day 7, Gi cells are sufficient and optimal for implantation, at day 8 St cells are sufficient and optimal for implantation, and as of day 10 Cl cells are sufficient and optimal for implantation. All other cells are not within an acceptable growth rate and would need to have increased levels of platelet lysate added to the culture medium to ensure optimal growth.

Example 2

Patient MSC Growth is Dependent on Patient's Health

MSCs were harvested from individuals having osteoarthritis and grown as described in Example 1. Growth rates for each patient's cells were determined as well as overall yield. Harvested MSCs were grown on varying amounts of platelet lysate (5-10%) and plotted over the course of 11 days (500% concentration of patient native platelet concentration and lysis using freezing). The data is shown graphically in FIG. 2, where MSC yield and rate of growth varied significantly. This Example illustrates the variability of growth found between patients and the need to optimize MSC growth rates.

Example 3

5% Platelet Lysate is Ineffective at Optimizing MSC Growth

MSC harvested from patients having osteoarthritis (slow growth MSC), as described in Example 1, were expanded using either 5% platelet lysate, 10% platelet lysate or 20% platelet lysate. As shown in FIGS. 3A-E, many cell lines grown with 5% platelet lysate were unable to show maximum expansion as compared to cells grown on 10-20% platelet lysate. Note that for most cell lines grown on 20% platelet lysate conditions showed only minimal expansion benefit as compared to 10% platelet lysate. However, it must be stressed that our experimental data shows that patients with OA have extremely variable expansion rates, with a few patients able to hit growth channel targets at 5%, most at 10%, and some requiring 20% supplementation. In addition, patients with other conditions such as avascular necrosis of the femoral head, fail expansion in even 10% lysate and require multiple modifications only determined via experimental protocol (see following example).

FIG. 4 further illustrates that MSCs harvested from osteoarthritis patients typically require higher levels of platelet lysate (10%+) to obtain optimum expansion. However, MSCs from healthy individuals having normal growth showed little variation under growth conditions of 5% or 10% platelet lysate.

The data in this Example illustrates that the conditions described by Doucet et al did not produce optimum expansion conditions under conditions where cells were harvested from osteoarthritic patients. These cells required higher percent platelet lysate in the growth medium to show optimum expansion.

However, under conditions where the cells are harvested and show "fast growth type," the cells were able to grow under conditions of 5 or 10% platelet lysate.

Example 4

Illustrative Growth Channel for 5 Different Patients

Five patients donated MSCs as harvested in Example 1. Cells were grown using varying lysate concentrations and cell number calculated. Cell growth data is shown in FIG. 5, where a cell growth channel of the present invention is overlayed. Cells able to expand within the cell growth channel parameters are considered optimal and ready for use in a target patient, whereas the cell growth for patient 5 would be a poor yield with minimal chances of clinical success. As such, platelet lysate based moderation of the cells' growth conditions should be used to obtain cell growth within the recited growth channel. In addition, the culture decisions already described based on cell density, culture pattern, and morphology would also need to be applied.

Example 5

MSC Cell Surface Antigens Present When Cells are Grown Within Growth Channel Parameters MSC were harvested and expanded using embodiments described herein and in Examples 1 and 2. To determine the phenotype of the cultured cells they were incubated with fluorescently labeled monoclonal antibodies (mAbs) directed against known stem cell surface antigens (MAbs used are listed in Table 1 and 2).

The expression level of the cell surface antigens on the cultured cells from 2 subjects was analyzed using FACSCalifur flow cytometer. Results are provided in Tables 1 and 2.

TABLE 1

| Surface Antigen | Mean Fluorescence Intensity | | |
| --- | --- | --- | --- |
| | Subject 1 | Subject 1 + HA | Subject 2 |
| CD14 | 5.78 | 4.66 | 5.05 |
| CD29 | 216.56 | 221.47 | 243.44 |
| CD31 | 7.18 | 5.68 | 5.21 |
| CD44 | 775.36 | 828.8 | 543.91 |
| CD45 | 5.46 | 5.73 | 5.4 |
| CD59 | 1712.53 | 1684.87 | 1412.54 |
| CD90 | 1222.7 | 1149.04 | 764.27 |
| CD106 | 22.87 | 21.31 | 19.06 |
| CD166 | 149.1 | 144 | 93.69 |
| CD73 | 1653.22 | 1688.02 | 1438.74 |
| CD105 | 1178.26 | 1169.62 | 1671.74 |

TABLE 2

| Surface Antigen | % Positive | | |
|---|---|---|---|
| | Subject 1 | Subject 1 + HA | Subject 2 |
| CD14 | 0.66 | 0.36 | 0.5 |
| CD29 | 99.93 | 99.49 | 99.51 |
| CD31 | 2.17 | 1.18 | 0.75 |
| CD44 | 99.9 | 99.44 | 99.49 |
| CD45 | 0.77 | 0.64 | 0.64 |
| CD59 | 99.34 | 99.76 | 99.5 |
| CD90 | 99.96 | 99.96 | 99.99 |
| CD106 | 42.93 | 41.03 | 27.73 |
| CD166 | 99.76 | 99.22 | 98.05 |
| CD73 | 99.94 | 99.84 | 99.76 |
| CD105 | 99.94 | 99.63 | 99.65 |

Table 1 shows the mean fluorescence intensity (MFI) for each target cell surface antigen. The percent positive value for each cell surface antigen is listed in Table 2. As shown in Table 2, greater than 99% of the cells optimized for implantation into a target patient expressed CD29, CD44, CD59, CD73, CD90, CD105 and CD166. Conversely, few cells expressed CD14, CD31, CD45 and CD106 which are not considered cell surface antigens generally present on the cells having optimal capacity for implantation into a target patient.

Example 6

MSC Implantation Using Embodiments Herein Provide for In Vivo Osteochondral Cartilage Replacement A bone marrow sample was obtained from a 57 year old patient needing cartilage replacement to correct a defect in the knee. The bone marrow was harvested and MSCs isolated using the methods described in Example 1. Cells were grown on 10-20% platelet lysate over the course of 6 passages to obtain 10 million cells. Cells were maintained in the growth channel of the present invention. Cells were then implanted into the site using the autologous MSCs.

Figure 6B:
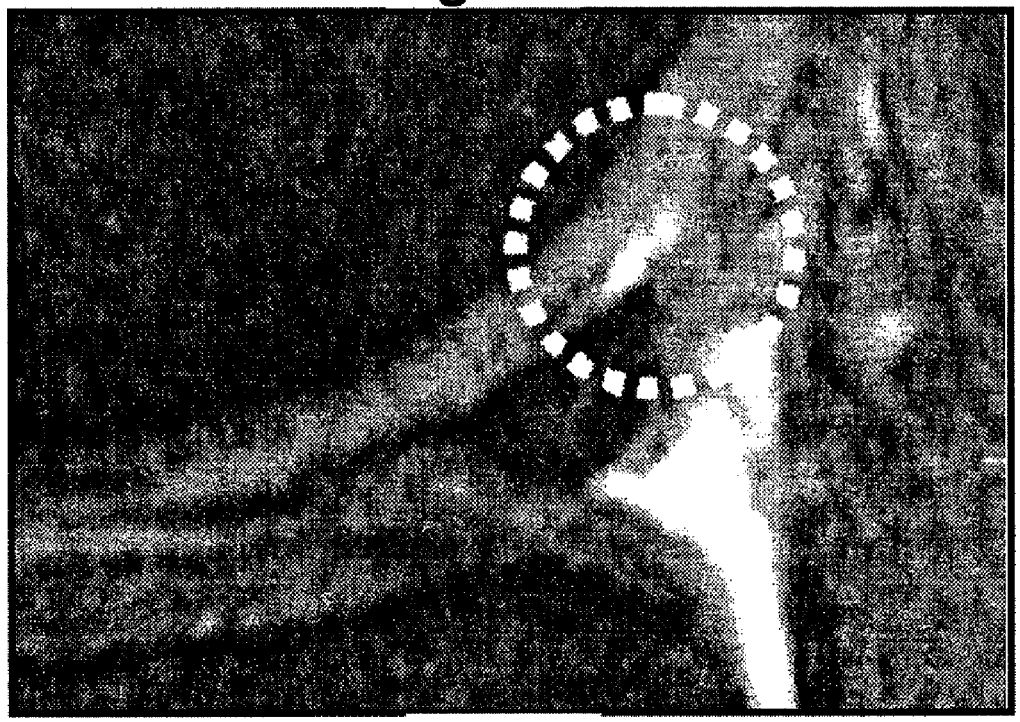

FIGS. 6(A&B) show sagittal Fast Spin Proton Density images from a 3.0 T MRI. The cartilage defect in the posterior weight bearing surface of the lateral femoral condyle is shown (A). After 39 days the image was re-taken and the cartilage defect has been filled (see FIG. 6B). The data from the Example shows the effectiveness of using the methods and compositions described herein to correct large cartilage defects at target sites.

Example 7

Timing of Higher Level Platelet Lysate Can Add Growth Momentum to Allow Slow Grower Types of MSCs to Hit Growth Channel Targets The following Example illustrates the concept that altering platelet lysate concentration during the course of ex vivo expansion dramatically improves MSC yield. A 20% platelet lysate concentration ("lysate boost") was used in the initial expansion culture as cells emerged out of colony formation. Four patient cell populations were tested, symbolized as Re, Gi, Ve and Ca. Growth conditions were monitored and are shown in Table 3 and FIG. 7.

Of the four patients listed in Table 3, note that for Gi and Ve, the MSC fold increase in cell growth per passage was dramatically improved. For subject Gi the sum of fold increase per passage increased from 9.74 to 12.96 when the 20% lysate boost was used. For Re this metric almost doubled from 6.88 to 10.34. Of note, both of these patients are in the target demographic for regenerative therapies with MSCs (diagnosed osteoarthritis (OA) and in $5^{th}$ and $6^{th}$ decades of life). For the younger subject, Ve (without known OA), there was only a slight improvement in the sum of the fold increase per passage (5.0 to 5.7). In the oldest subject in the $7^{th}$ decade of life and with severe multi-joint OA, there was also only a mild improvement in this measure (5.08 to 5.13).

Since half of the four subjects had a marked improved yield and the other two subjects had no decrement in yield and saw very slight yield improvement, the methods and compositions described herein are valid for improving MSC yield in a cohort of OA patients in need of regenerative medicine.

Example 8

Growth Conditions for a Patient in Need of MSC Implantation 44 year old white female with avascular necrosis had 10 cc of marrow drawn from each PSIS and the cells processed per this invention. Her nucleated cell yield was very poor and her cells were grown in monolayer with 10% lysate, but failed to expand beyond the second passage. The patient was returned and an altered marrow draw technique was used to draw three small aliquots of marrow from the left and right PSIS and then cells were boosted with 20% platelet lysate while still in colony formation culture and then grown in 20% lysate. FIG. 8 demonstrates both cell expansion graphs and highlights that many patients with this disorder require a altered marrow draw techniques to improve nucleated cell count, a lysate boost during colony formation culture, and much higher platelet lysate concentrations while in the monolayer culture expansion phase.

Example 9

Direct Injection of Cells of the Present Invention 37 year old white female with a 9 month old fracture of the humerus treated with Open Reduction and External Fixation and a bone stimulator. This fracture went onto significant non-union as demonstrated in FIG. 10a. The patient had 100 cc of marrow drawn from each PSIS and the MSC's were isolated and grown in 10% platelet lysate. These were then percutaneously implanted into the fracture non-union site via sterile trocar under fluoroscopic guidance. FIG. 10b shows significant healing of the non-union at 5 weeks post injection of cells. This example illustrates the in-vivo osteogenic capabilities of the MSC's expanded with this invention.

Example 10

Knee Cartilage Replacement 43 year old white male with severe degenerative disease of the medial compartment of the knee showing significant degradation of the medial anterior meniscus. FIG. 11A shows a 3.0T proton density sagittal MRI image where the significantly degenerated medial meniscus is almost entirely absent anteriorly. FIG. 11B is 3 months post after percutaneous implantation of MSC's obtained and expanded per the growth channel methods described herein. FIG. 11B shows regeneration of the meniscus and subsequent 3-D image volume analysis demonstrated a 32.5% increase in meniscus volume. Note that meniscus regeneration occurred in the inner portion of the meniscus, in what is known as the "white" or "avascular" zone. For this to occur, vessels would have to be brought to the area. This occurred either as a property of this specific cell line or more likely due to the platelet lysate injections provided to the joint after implantation of cells. For example, it is well known that platelet lysate has significant level of VEGF capable of causing neovascularization.

TABLE 3

Fold Increase in Cell Growth Per Passage
Fold Increase In Cell Growth/Passage

| Passage No. | Re 10% PL/ 20% PL | Gi 10% PL/20% PL | Ve 10% PL/ 20% PL | Ca 10% PL/20% PL |
|---|---|---|---|---|
| P1 | 3.6/5 | 5.6/5.4 | 2.6/2.6 | 3.1/1.95 |
| P2 | 1.48/2.19 | 2.18/3.36 | 2.4/3.1 | 1.98/3.18 |
| P3 | 1.8/3.15 | 1.96/4.2 | | |

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

This specification contains numerous citations to patents, patent applications, and publications; each is hereby incorporated by reference for all purposes.

What is claimed is:

1. A method of expanding mesenchymal stem cells (MSC) in vitro for use in an implant to regenerate cartilage, the method comprising:
   (a) obtaining mesenchymal stem cells (MSCs) from an older patient in the $5^{th}$ to $7^{th}$ decade of life who is diagnosed with osteoarthritis, avascular necrosis, or severe degenerative joint disease;
   (b) expanding the MSCs with a growth medium comprising the patient's platelet lysate in an initial amount of 10% of the growth medium for at least one passage to obtain at least 10 million to 100 million cells;
   (c) determining whether the MSCs of step (b) are outside the scope of one or more of the following parameters:
      (i) a doubling time of about 1 to about 3 days;
      (ii) cellular confluence greater than about 27 calculated according to the equation Surface area×(% Confluence)/Cell Number;

(iii) random distribution of MSCs as a monolayer culture; or
      (iv) greater than 30% of MSCs without a spindle shape; and
   (d) adjusting the growth medium in the following passages wherein the MSC are outside of the scope of at least one parameter in step (c) by increasing the amount of platelet lysate in the growth medium to between 15-20% platelet lysate;
   wherein the expanded MSCs are capable of regenerating new cartilage when implanted into the patient at a site in need thereof no later than the tenth ex-vivo passage.

2. The method of claim 1 further comprising implanting the expanded MSC into a site in need thereof and in-vivo monitoring of the site in the patient after implantation of expanded MSCs.

3. The method of claim 1 further comprising injecting platelets or platelet lysate directly into the site of the patient during or after implantation of the expanded MSCs to further facilitate MSC expansion.

4. The method of claim 1 wherein the MSCs are expanded up to a $7^{th}$ ex-vivo passage.

5. The method of claim 1 wherein the site in need thereof is a degenerated joint.

6. The method of claim 1 wherein the obtaining MSCs from the patient comprises a marrow draw technique, wherein the marrow draw technique comprises taking one or more 1-10 ml draws to boost MSC yield.

7. The method of claim 2, wherein the in-vivo monitoring includes direct visualization of the site being treated surgically and/or arthroscopically.

* * * * *